United States Patent
Sakiewicz

(10) Patent No.: US 7,815,588 B2
(45) Date of Patent: Oct. 19, 2010

(54) METHOD AND DEVICE FOR REVERSING LINES IN THE PROCEDURE OF HEMODIALYSIS

(76) Inventor: Paul Sakiewicz, 5877 S. Kenton Way, Englewood, CO (US) 80111

( * ) Notice: Subject to any disclaimer, the term of this patent is extended or adjusted under 35 U.S.C. 154(b) by 235 days.

(21) Appl. No.: 11/680,903

(22) Filed: Mar. 1, 2007

(65) Prior Publication Data

US 2007/0287948 A1 Dec. 13, 2007

Related U.S. Application Data

(60) Provisional application No. 60/804,147, filed on Jun. 7, 2006.

(51) Int. Cl.
*A61M 37/00* (2006.01)
(52) U.S. Cl. ............... 604/5.01; 251/4; 251/231
(58) Field of Classification Search ........... 604/4.01, 604/5.01, 5.04, 6.1; 210/645, 646; 422/44; 137/475, 561 A, 597, 625.43; 251/4–10, 251/78, 149.2, 231
See application file for complete search history.

(56) References Cited

U.S. PATENT DOCUMENTS

| | | | | |
|---|---|---|---|---|
| 715,266 | A * | 12/1902 | Heston | 137/625.23 |
| 3,419,827 | A * | 12/1968 | Webb | 333/106 |
| 3,697,418 | A * | 10/1972 | Johnson | 210/647 |
| 5,595,182 | A | 1/1997 | Krivitski | |
| 5,685,989 | A | 11/1997 | Krivitski et al. | |
| 5,687,764 | A * | 11/1997 | Tanaka et al. | 137/625.43 |
| 5,830,365 | A * | 11/1998 | Schneditz | 210/739 |
| 5,894,011 | A | 4/1999 | Prosl et al. | |
| 6,153,109 | A | 11/2000 | Krivitski | |
| 6,308,737 | B1 * | 10/2001 | Krivitski | 137/597 |
| 6,514,419 | B2 | 2/2003 | Krivitski | |
| 6,536,464 | B1 * | 3/2003 | Lum et al. | 137/337 |
| 6,726,647 | B1 * | 4/2004 | Sternby et al. | 604/6.09 |
| 6,743,193 | B2 * | 6/2004 | Brugger et al. | 604/6.1 |
| 6,926,838 | B2 | 8/2005 | Krivitski | |
| 7,384,543 | B2 * | 6/2008 | Jonsson et al. | 210/97 |
| 7,500,958 | B2 * | 3/2009 | Asbrink et al. | 604/6.1 |
| 2003/0138348 | A1 * | 7/2003 | Bell et al. | 422/44 |
| 2004/0210180 | A1 | 10/2004 | Altman | |
| 2004/0243046 | A1 * | 12/2004 | Brugger et al. | 604/4.01 |
| 2005/0145549 | A1 * | 7/2005 | Jonsson et al. | 210/97 |
| 2005/0203457 | A1 | 9/2005 | Sinego | |
| 2006/0049267 | A1 | 3/2006 | Lum et al. | |
| 2006/0052715 | A1 | 3/2006 | Krivitski | |
| 2006/0064025 | A1 | 3/2006 | Kraemer | |

FOREIGN PATENT DOCUMENTS

WO WO2005/061043 7/2005

OTHER PUBLICATIONS

International Search Report for International (PCT) Patent Application No. PCT/US07/70221, mailed Dec. 5, 2007.
Written Opinion for International (PCT) Patent Application No. PCT/US07/70221, mailed Dec. 5, 2007.
International Preliminary Report on Patentability for International (PCT) Patent Application No. PCT/US07/70221, mailed Dec. 24, 2008.

* cited by examiner

*Primary Examiner*—Tatyana Zalukaeva
*Assistant Examiner*—Benedict L Hanrahan
(74) *Attorney, Agent, or Firm*—Sheridan Ross P.C.

(57) ABSTRACT

A device and method for selectively controlling the direction of blood flow to and from the patient during hemodialysis is provided. Specifically, the device and method reverse flow between four fluid lines without changing connections between a patient and a hemodialysis machine. Advantageously, the blood is subjected to minimal stresses as it passes through the switching device.

28 Claims, 20 Drawing Sheets

METHOD AND DEVICE FOR REVERSING LINES IN THE PROCEDURE OF HEMODIALYSIS

CROSS REFERENCE TO RELATED APPLICATIONS

This Application claims the benefit of U.S. Provisional Application No. 60/804,147, filed Jun. 7, 2006, the entire disclosure of which is hereby incorporated herein by reference.

FIELD OF THE INVENTION

The present invention relates generally to switching devices and methods used to reverse fluid flow in (or within) lines. More specifically, the flow switching methods and devices can be used in the procedure of hemodialysis.

BACKGROUND

In medicine there are many applications requiring the control of the flow of fluids such as, for instance, of biological fluids. One such application, for example, is the control of the blood flow during an extracorporeal blood treatment otherwise known as hemodialysis. During hemodialysis treatment, a patient's vascular system is connected to a hemodialysis machine for sessions that can last several hours. This connection forms a blood circuit, whereby blood is drawn from the patient through a needle connected to a flexible blood line, cycled through a hemodialysis machine that removes waste products including water, urea, and other impurities of the blood, and returned to the patient via a second blood line and needle.

In order to withdraw blood from a patient, a blood access is commonly created in the nature of an arterio-venous shunt, refereed to as a fistula. During the blood treatment, blood is taken out from the fistula at an upstream position of the fistula and is returned to the fistula at a downstream position.

Alternatively a polytetrafluoroethylene (PTFE) can be used to access a patient's bloodstream. A PTFE graft is an artificial blood vessel used to connect an artery to a vein. The material used for the graft is suitable for puncturing with needles to achieve the necessary access to the patient's blood system.

A third method of obtaining access to a patient's blood for hemodialysis is to use percutaneous catheters, which allow blood to be withdrawn from one lumen and returned by a second lumen. As can be appreciated there may be a number of other different ways to access a patient's blood for hemodialysis.

During the procedure of hemodialysis it is advantageous to operate with blood flows at the highest rates possible in order to maximize the efficiency of the treatment, while avoiding damage to the blood cells. One difficulty that can arise in chronic hemodialysis is maintaining adequate blood flow during treatment sessions. When flow rates decrease significantly, an attendant can sometimes restore adequate flow by switching the blood lines. In the past, the attendant would turn off the hemodialysis machine and physically switch the lines connecting the hemodialysis machine and patient. The line that was previously drawing blood from the patient and carrying it to the machine is switched such that it supplies blood from the machine to the patient. The other line that was previously supplying blood to the patient is then switched to draw blood from the patient. Once the lines are switched the hemodialysis machine is turned back on and the process continues.

There are several problems with physically switching the blood lines during hemodialysis. One problem is that the disconnecting and switching of lines is a time consuming process that further lengthens an unpleasant hemodialysis procedure for the patient. Another problem is that the switch may cause bleeding and allow air to enter the lines. Disconnecting the lines also breaks the microbe barrier, which increases the possibility of infection. Thus, blood lines are often not switched during hemodialysis treatment, unless it is absolutely necessary.

There have been some attempts to solve the problem associated with switching blood lines during hemodialysis. For example in U.S. Pat. No. 5,894,011 to Prosl et al., (the entire disclosure of which is hereby incorporated herein by this reference), relates to a device for selectively controlling the direction of blood flow to and from the patient during hemodialysis and comprises two interlocking disks that rotate in relation to each other without separating. The two disks have fluid fittings that allow the bloodlines attached to the patient to connect to one of the disks and the blood inlet and outlet for the hemodialysis machine to connect to the other. In the center of each fluid fitting is a channel that aligns to a corresponding channel in the other disk. The disks rotate between two fixed relative positions, referred to as preferred alignments. The preferred alignments are such that the line drawing blood from the patient in the first preferred alignment becomes the line returning blood to the patient in the second preferred alignment, and the line returning blood to the patient in the first preferred alignment becomes the line drawing blood from the patient in the second preferred alignment. Thus, blood flow between the two patient lines can be reversed without reversing flow through the two unit lines and the connected hemodialysis machine.

Problems common to the above devices having rotating bodies in direct contact with blood include, for example, a risk that the blood clots or clogs in the space between the two rotatably connected parts and that blood cells may be damaged during rotation of the rotatably connected parts. Many patients who are dependent on dialysis also have a low production of blood cells. Thus, it is important to avoid damaging blood cells during dialysis. Thus, multiple reversals of blood flow is not advisable using such devices having rotating bodies.

Another problem with devices having rotating bodies is the cost of producing such a device is significantly large considering such devices are one-time use devices because sterilization of such components is impractical. It is preferable to keep costs of preferred disposable devices to a minimum if they are to become commercially viable.

Also, PCT Patent Application No. WO2005/061043 to Gambro Lundia AB, (the entire disclosure of which is hereby incorporated herein by this reference), shows a further attempt to provide a solution for the switching of lines problem associated with hemodialysis. The switching device in the '043 application includes a deformable portion having four ports, two of which are connected to the patient and two of which are connected to the hemodialysis machine. The device operates in a first and second clamping position, where a wedge squeezes the deformable portion in different directions to change the flow of blood. One problem associated with the device in the '043 application is that the wedge used to interact with the deformable portion has a straight edge. The straight edge causes the blood to have a radical change of direction when it enters the switching device, which may damage the blood cells or cause blood clotting in the device.

The wedge set forth in the Gambro Lundia PCT application is designed to have a straight edge because of the configuration of the four ports of the device. Namely the four ports do not join at a single point but rather form a connection network that resembles a square. The square connection is divided into two when the wedge intersects the deformable portion. As noted above, the problem with this particular configuration is that the blood undergoes non-trivial stresses as it enters the switching mechanism, thus potentially exposing blood cells to undesired shear forces.

Furthermore potential blood stagnation occurs within the device in certain portions, such that there is risk for blood clotting to occur. Blood clots within any blood tubing is very worrisome because those clots could either go towards the patient, potentially leading to major problems, or less problematic to the dialysis machine, where it nevertheless can interfere with the quality of the dialysis treatment.

SUMMARY

These and other needs are addressed by various embodiments and configurations of the present invention. The present invention is directed generally to a device and method for switching fluid flow to and from a patient without substantially damaging the fluid. More specifically, the present invention allows blood flow direction to be switched during the process of hemodialysis relatively quickly and easily and without substantial or significant shear forces being experienced by blood cells.

In accordance with one embodiment of the present invention, a device is provided for switching the direction of fluid flow to and from a patient. The device comprises the following:

(a) an intersection point between a first, second, third, and fourth port;

(b) an occlusion mechanism having a radius of curvature for operatively adapting the intersection such that in a first position, the first and second ports are fluidically connected by the intersection and the third and fourth ports are fluidically connected by the intersection and in a second position, the first and fourth ports are fluidically connected by the intersection and the second and third ports are fluidically connected by the intersection.

The occlusion mechanism is advantageously designed, in at least one embodiment, to apply a minimal force to blood cells or the like as they pass through the switching device. The radius of curvature affords for a smooth transition between one port and another port. The curved occlusion mechanism also creates a near perfect channel between adjacent ports, which helps inhibit blood from clogging at the intersection during the hemodialysis procedure. The near perfect channel also helps facilitate substantially laminar flows of the blood through the intersection.

In one embodiment, the occlusion mechanism is equipped with two separating members, each of which has an inwardly directed radius of curvature. To have an inwardly directed radius of curvature means that the radius of curvature extends toward the intersection, whereas an outwardly directed radius of curvature would be a radius of curvature that extends outwards from the intersection. In other words, an inwardly directed radius of curvature is similar to a concave optical lens whereas an outwardly directed radius of curvature is similar to a convex optical lens.

More specifically, in one embodiment, one or both of the separating members comprise a first end and a second end with a middle portion therebetween. The middle portion of the separating member is generally thinner than the ends of the separating member resulting in a convex shape of the separating member.

In accordance with one embodiment, when the occlusion mechanism is not engaging the intersection, the intersection is a common space that is shared by all four ports. When the occlusion mechanism engages the intersection, the area of the intersection changes form to separate a set of two ports from the other set of two ports, thus completing the extracorporeal circuit. The blood flows from the patient through the intersection in one direction via the first set of two ports. Thereafter, the blood flows to a filter or the like to be treated. Thereafter, the blood flows through the intersection in another direction via the second set of two ports and back into the patient. The occlusion mechanism can be switched to a second operational mode where two different ports are connected to form the first set and the other two ports are connected to form the second set. The blood continues to flow from the intersection to the filter and back to the intersection via the same ports. However, the ports that correspond to lines connected to the patient are switched, meaning that the line that was previously drawing blood from the patient is now carrying blood to the patient and vice versa.

It is one aspect of the present invention to keep costs of producing such a switching device low. In accordance with at least one embodiment of the present invention, the occlusion mechanism comprises a base member that can be formed from any suitable type of material including, without limitation, plastic, ceramic, steel, etc. The occlusion mechanism further comprises a first and second separating member that are attached or otherwise secured to the base member by a pivot assembly or the like. In the first operational mode (i.e., the first position), the first of the separating members is pivoted down onto the intersection to separate the four ports into a first and second set of ports. When it is desired to switch blood flow to/from the patient, the first separating member may be pivoted up and the second separating member may be pivoted down, thus separating the four ports into a third and fourth set of ports.

In an alternative embodiment, the occlusion mechanism may comprise a single separating member that can be moved relative to the intersection such that it can interact with the intersection from two different directions. For example, the separating member can engage the intersection with a first orientation in a first mode of operation. The separating member can then be lifted and/or rotated and placed in a second orientation relative to the intersection for a second mode of operation.

In accordance with one embodiment, the occlusion mechanism comprises a pair of separating members that can be brought together about the intersection. Each of the separating members may have a first radius of curvature in a first plane and a second radius of curvature in a second plane. Thus, when the two separating members are brought together, their shape substantially resembles half of a pipe bending in a certain direction. The use of a pair of separating members helps to create a smooth transition between adjacent ports at the intersection, thus decreasing the amount of stress applied to blood cells.

In accordance with at least one embodiment, the blood flow may be reversed to allow an attendant to either measure access blood flow online or to allow for more blood flow for hemodialysis. More specifically, the switching device affords the capability of reversing lines without any significant attendant time involved. Moreover, the switching device can be configured such that the occlusion mechanism is coupled to a button or switch that allows an attendant to easily switch the operational positions of the occlusion mechanism. With the push of a button, blood flow to/from the patients access can be reversed as described, and access blood flow can be measured within a few minutes. In accordance with one embodiment of the present invention, the switching device may be incorporated into a hemodialysis machine. The machine may be fully integrated to comprise all of the functionality necessary to perform hemodialysis and switch blood flow if required. The machine may comprise a switching device having four ports. Two of the ports may be connected to a filter or some other type of fluid treatment device. The other two ports may be connected to a patient (i.e., a patient's vascular system). The four ports may be joined at a common intersection whose configuration can be changed by an occlusion mechanism. The occlusion mechanism may be coupled to a controller (i.e., a button, lever, switch, control panel, touch screen interface, etc.) on the face of the machine. Once the patient is connected to the hemodialysis machine, the hemodialysis process can begin. The machine may further comprise a display device that allows the attendant to read measured information relating to the hemodialysis procedure (e.g., blood flow, blood pressure, heart rate, and the like). Based on the information displayed the display device may instruct the attendant to switch blood flow to/from the patient. With a simple press of a button, the occlusion mechanism can switch positions and reverse the flow of blood.

Blood flow is generally reversed to measure access blood flows. In U.S. Pat. Nos. 5,595,182; 5,685,989; 6,153,109; 6,514,419; 6,926,838; and 2006/052715 to Krivitski, the entire disclosures of which are hereby incorporated herein by this reference, various methods of measuring cardiac output via an extracorporeal cardiopulmonary support circuit are provided. For example, the method described in the '715 publication includes temporarily reversing flow through an arterial line of the extracorporeal and passing an indicator through the reversed cardiopulmonary circuit. Using the indicator, a dilution curve is measured in the arterial line of the extracorporeal circuit during the reversed flow, and access blood flow is determined corresponding to the measured dilution curve. According to embodiments of the present invention, the act of temporarily reversing blood flow becomes relatively easy and safe when using a switching device as described herein.

In accordance with further embodiments of the present invention, methods of measuring cardiac output may also be provided. In such an embodiment, the lines between to the hemodialysis machine do not need to be reversed; however, according to embodiments of the present invention, the Cardiac Output (CO) could be checked easily arid practically using the device of the present invention. Then access blood flow could be checked (e.g., by keeping the lines in normal configuration for CO and then switching to the reversed configuration for access blood flow), thereby enabling the possibility of diagnosing high output heart failure and suspecting such a problem if the ratio of access blood flow to CO is >0.3, for example.

Another method described by Krivitski includes temporarily reversing blood flow as it relates to the hemodialysis circuit as described previously then injecting the indicator on the venous side of the patient. Recirculation is then determined by measuring the amount of indicator passing through the upstream (arterial side when flows are reversed) of the circuit. This amount of recirculation is used in the following equation:

$$[(1-R)/R] \times QB = AF$$

where R is the measured recirculation according to the indicator, QB is the pump speed of the hemodialysis machine, and AF is the access flow rate in the patient. If R can be measured by reversing the flow and QB is a known parameter, then AF can be calculated. For example, if recirculation R is measured to be about 30% or 0.3 and the known pump QB speed is approximately 300 ml/min, then the access flow rate AF can be determined to be about 700 ml/min.

In an alternative embodiment, the hemodialysis machine may analyze the patient information and automatically determine that it is time to switch the blood flow by for instance recognizing pressure changes or speed of blood circuit flow within the dialysis circuit, which would make it more beneficial to have the dialysis treatment run in the reversed position. The hemodialysis machine can then automatically switch the position of the occlusion mechanism, resulting in a blood flow reversal. The automation of the hemodialysis procedure can introduce significant time savings to attendants and doctors alike.

One aspect of the present invention is to provide a switching device that can be used to reverse the blood flow during hemodialysis multiple times. The switching device has a minimal negative impact on blood flowing through it. Because the switching device can be used to switch blood flow direction multiple times, access blood flow rates can be monitored on a regular basis without placing an excessive burden on attendants/doctors. It is in fact important to get reproducible results and measure dialysis access blood flow at least twice to arrive at a reliable result. This device allows for that process to occur at different times during the dialysis treatment, while with other devices it is not advisable to switch the flow multiple times, even if needed. The more often a blood flow rate can be measured, the more likely access problems can be detected early on. The advanced notice of access problems can help a physician make better decisions about how to remedy the access problems.

These and other advantages will be apparent from the disclosure of the invention(s) contained herein. The above-described embodiments and configurations are neither complete nor exhaustive. As will be appreciated, other embodiments of the invention are possible utilizing, alone or in combination, one or more of the features set forth above or described in detail below.

DETAILED DESCRIPTION

The invention will be illustrated below in conjunction with an exemplary hemodialysis system. Although well suited for use with, e.g., a system using fluid lines, pumps, and filters, the invention is not limited to use with any particular type of fluid manipulation device or system. Those skilled in the art will recognize that the disclosed devices may be used in any application where it is desirable to change the direction of flow of a fluid without changing connections of lines at their source.

Figure 1:
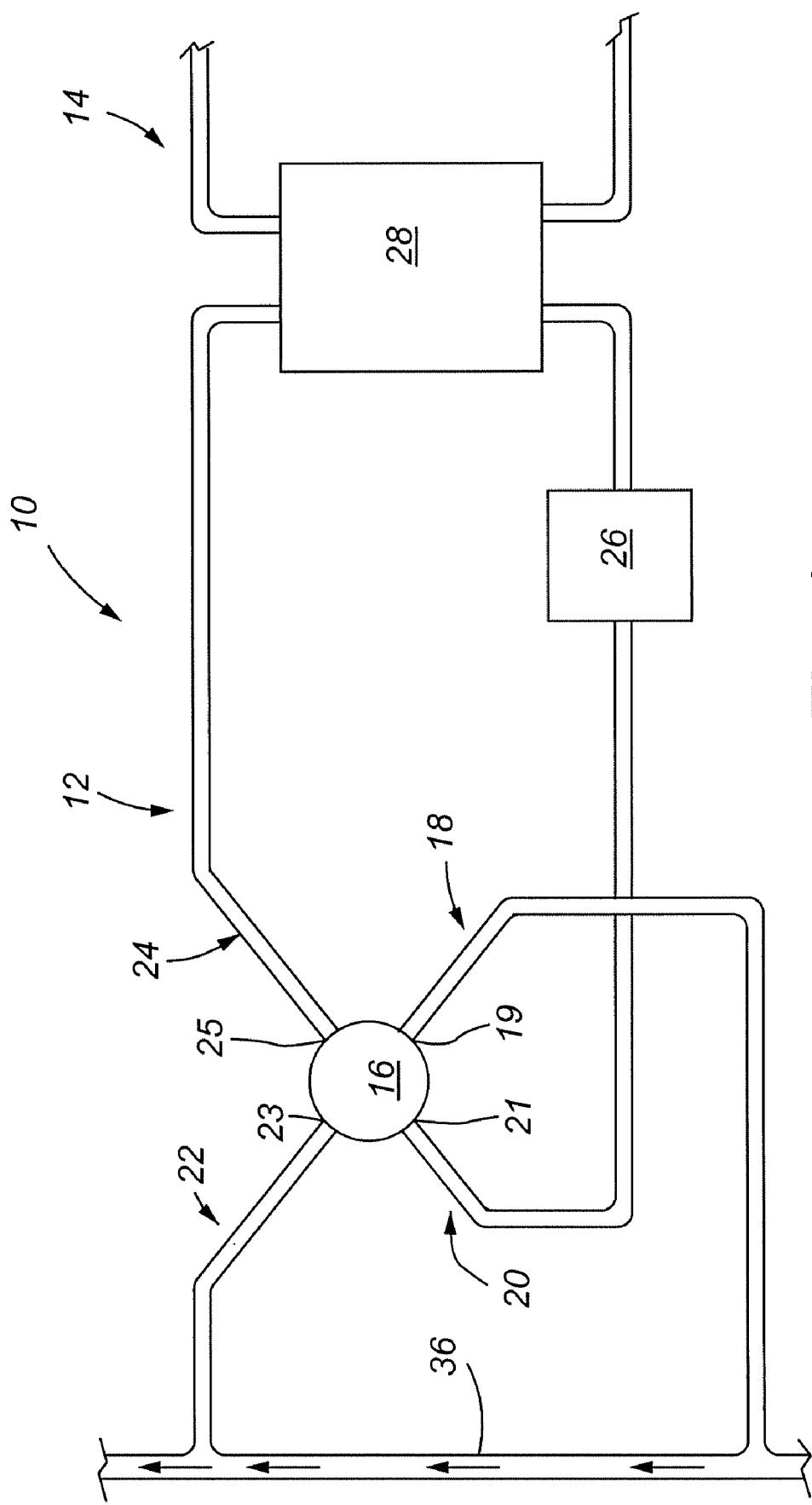
FIG. 1 depicts an extracorporeal circuit of a hemodialysis machine in accordance with some embodiments of the present invention.

FIG. 1 illustrates exemplary blood treatment equipment 10 comprising a fluid distribution side 12 and a waste treatment side 14 in accordance with at least one embodiment of the present invention. The fluid distribution side 12 is connected to the waste treatment side 14 by a filter 28 or similar type of fluid treatment unit. The filter 28 may comprise a semipermeable membrane separating two chambers, each chamber corresponding to a side of the filter 28. In one embodiment, the filter 28 comprises a dialyzer, although other suitable types of treatment units may be employed including a hemofilter, a hemnodiafilter, an ultrafilter, or a plasmafilter, depending upon the type of treatment desired for the blood. The filter 28 acts to remove waste and other foreign debris from the fluid on the distribution side 12 and dispose of it through the waste treatment side 14.

The distribution side 12 comprises an extracorporeal circuit when connected to a patient or the like. A switching device 16 facilitates the reversal of blood flow in a patient during the hemodialysis procedure. The switching device 16 serves as a connection of four lines. The first line 18 corresponds to the arterial-patient (AP) side and in a first operational mode draws blood from the patient. In a second operational mode the first line 18 carries blood to the patient from the switching device 16. The first line 18 enters the switching device 16 at a first port 19, which corresponds to the AP side of the switching device 16. The second line 20 corresponds to the arterial-machine (AM) side and in both the first and second operational modes, supplies blood to the dialysis machine 10, and more specifically to the filter 28. The second line 20 is connected to the switching device 16 at a second port 21, which corresponds to the AM side of the switching device 16. The third line 22 carries blood to the patient in the first operational mode and corresponds to the venous-patient (VP) side. In the second operational mode the third line 22 draws blood from the patient and carries it to the switch 16. The third line 22 is connected to the switch 16 by a third port 23, also referred to as the VP side of the switching device 16. The fourth line 24 carries blood from the filter 28 to the switching device 16 and corresponds to the venous-machine (VM) side. The fourth line 24 is connected to the switching device 16 by a fourth port 25, which corresponds to the VM side of the switching device 16.

In the first operational mode a pump 26 or similar type of pressure gradient producing device is used to draw blood from a patient through the first line 18. The blood flows from the first line 18 into the switching device 16, where it is directed into the second line 20. The blood then passes through the pump 26 and enters the filter 28 where toxins or other undesired elements are removed from the blood. The blood then exits the filter 28 via the fourth line 24 and enters the switch 16, where it is directed into the third line 22 that returns the blood to the patient.

In the second operational mode the configuration of the switch 16 is adjusted such that the blood is drawn from the patient via the third line 22. Blood enters the switch 16 from the third line 22 and is redirected to the second line 20. The second line 20 carries the blood to the filter 28 in the same direction as it entered the filter 28 in the first operational mode. The blood exits the filter 28 via the fourth line 24, again in a similar fashion to the first operational mode, where it is introduced to the switch 16. In the second operational mode, the switch 16 directs blood from the fourth line 24 to the first line 18 where it is sent back to the patient's blood stream.

The configuration of the switch 16 in the first operational mode is such that the AP port 19 is connected to the AM port 21 and the VP port 23 is connected to the VM port 25. In the second operational mode, the configuration of the switch 16 connects the VP port 23 to the AM port 21 and the AP port 19 to the VM port 24. This allows an attendant or the like to switch blood flows during hemodialysis without changing lines or changing the direction of fluid flow through the filter 28. As previously noted, the flow reversal may be desired to measure the blood flow in the patient or to induce additional blood flow.

Figure 2:
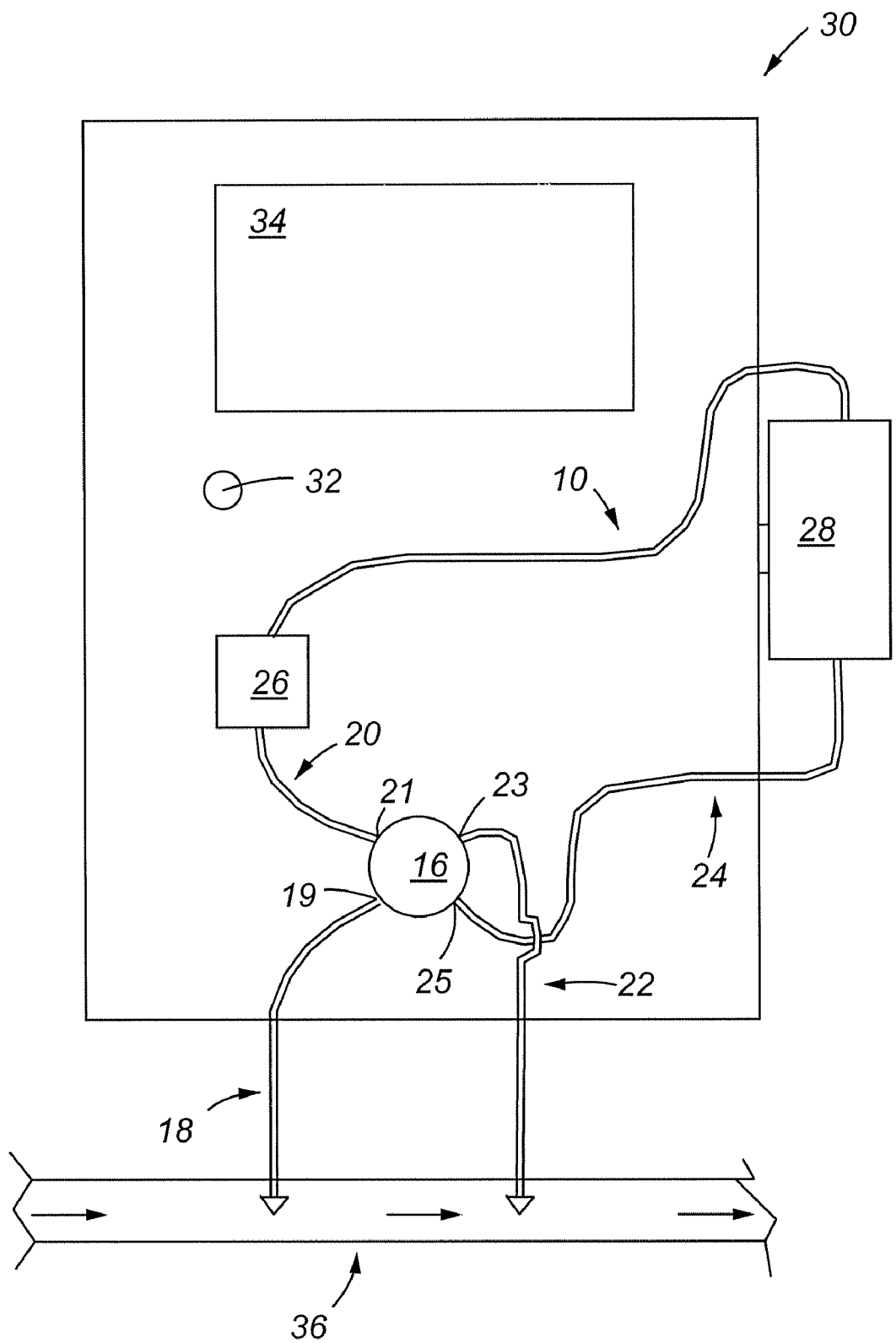
FIG. 2 depicts a hemodialysis machine in accordance with some embodiments of the present invention.

Referring now to FIG. 2, a hemodialysis machine 30 will be described in accordance with at least some embodiments of the present invention. The hemodialysis machine 30 comprises the blood treatment equipment 10 along with an actuator 32 and a display apparatus 34. The actuator 32 is coupled to the switching device 16 (either mechanically, electrically, or both) such that the orientation of the switching device 16 is changed when the actuator 32 is engaged.

For example, the first operation mode of the switching device 16 may correspond to a first position of the actuator 32 (e.g., button not depressed, lever/switch up, touch screen indicators, and so on) and the second operational mode of the switching device 16 may correspond to a second position of the actuator 32 (e.g., button depressed, lever/switch down, etc.).

During the hemodialysis procedure the attendant can monitor the patient's information on the display apparatus 34 and determine if the blood flow needs to be reversed. If the attendant decides that the blood flow should be reversed, the actuator 32 is engaged/disengaged thus changing the orientation of the switching device 16. When the orientation of the switching device is changed, the upstream portion of the patient's access 36 that was previously used to draw blood is used to supply blood back to the patient. Likewise, before the actuator 32 was engaged/disengaged blood was being provided to the patient's access 36 at the downstream portion of the access 36, whereas after the actuator 32 is engaged/disengaged blood is drawn from the downstream portion of the access 36.

The act of switching the orientation of the switching device 16 may be completed manually as described above, or may be done automatically by the hemodialysis machine 30. The hemodialysis machine may measure the patient's blood flow, blood pressure, and any other indicia related to hemodialysis and based on any changes to those readings, may switch the orientation of the switching device 16. For example, a threshold of blood pressure change within blood tubing to a sufficient degree as to potentially lead to damage of blood cells, may indicate that the blood flow needs to be reversed. In the event that the threshold is met or exceeded, the machine 30 automatically changes the orientation of the switching device 16 resulting in a reversal of blood flow. In an alternative embodiment, the blood flow may be reversed on a periodic basis to measure dialysis access blood flow rates. Because the blood flow rate can be measured multiple times during hemodialysis, early detection of access problems may be possible. Also, by automating the process of reversing blood flow entirely, an attendant can focus on more important issues like the patient's comfort and the like, rather than having to focus on reversing the flow of blood manually.

Figure 3:
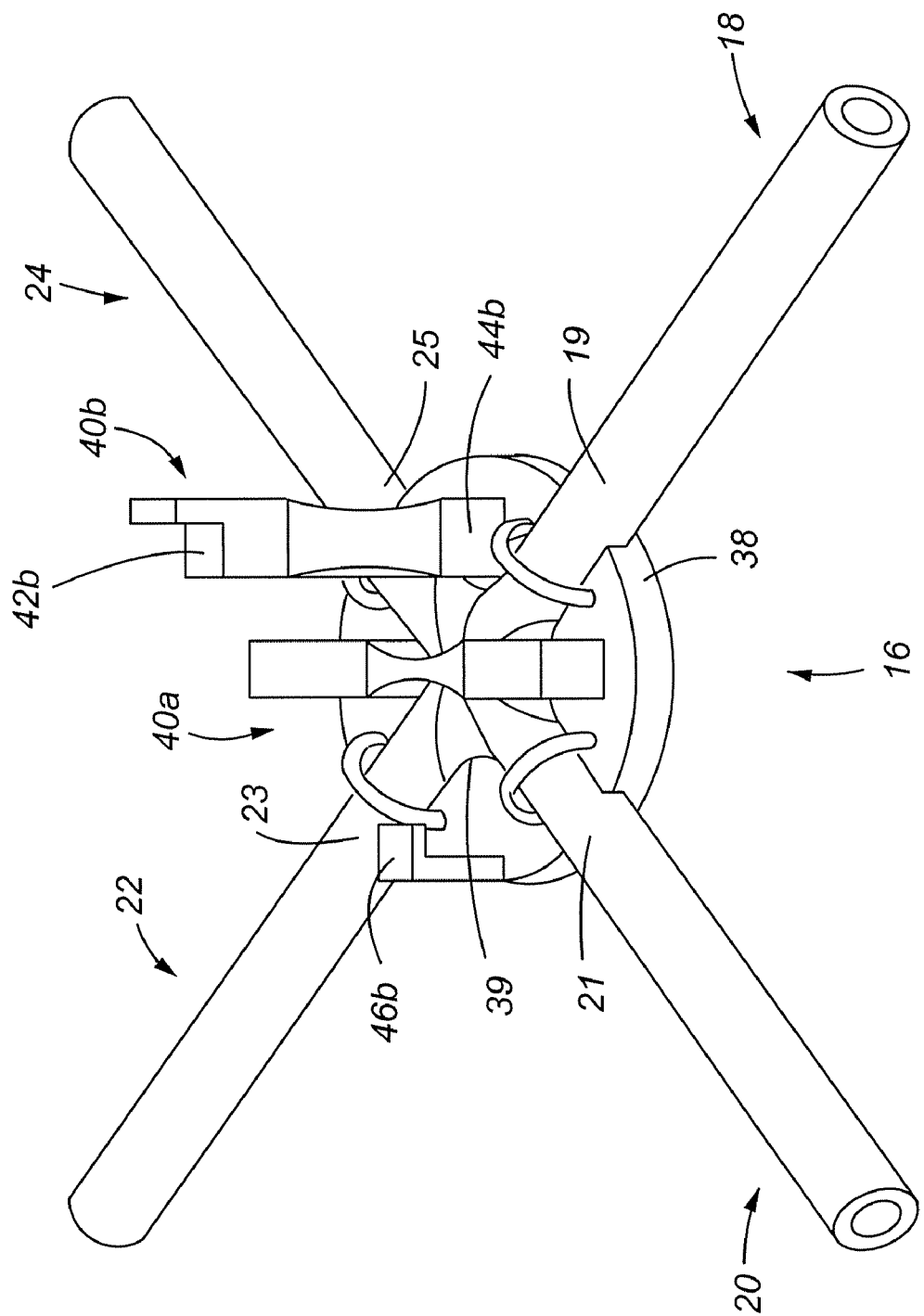
FIG. 3 depicts an occlusion member in accordance with some embodiments of the present invention.
Figure 4A:
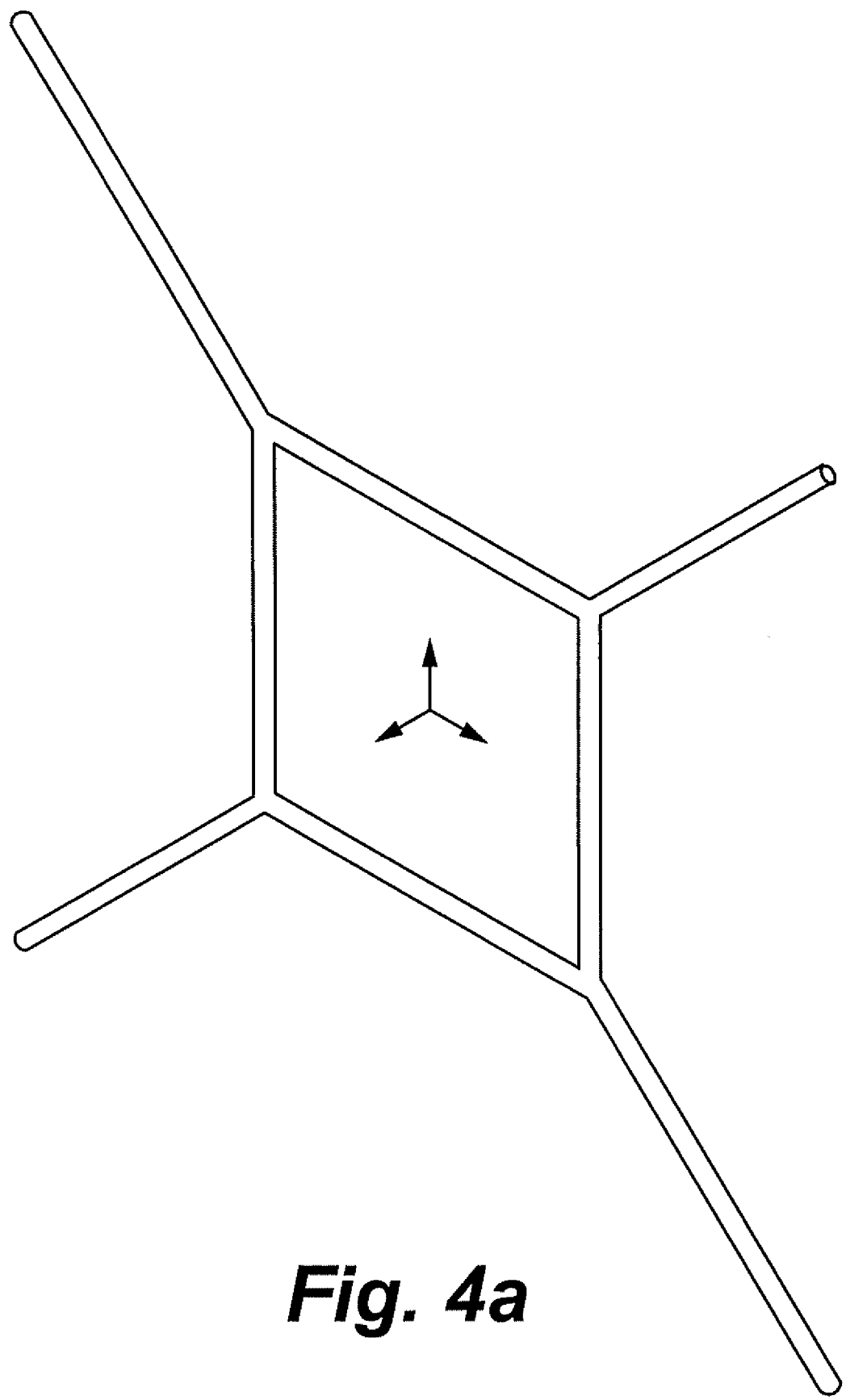
FIG. 4a depicts a first configuration of an intersection of four ports in accordance with some embodiments of the present invention.
Figure 4B:
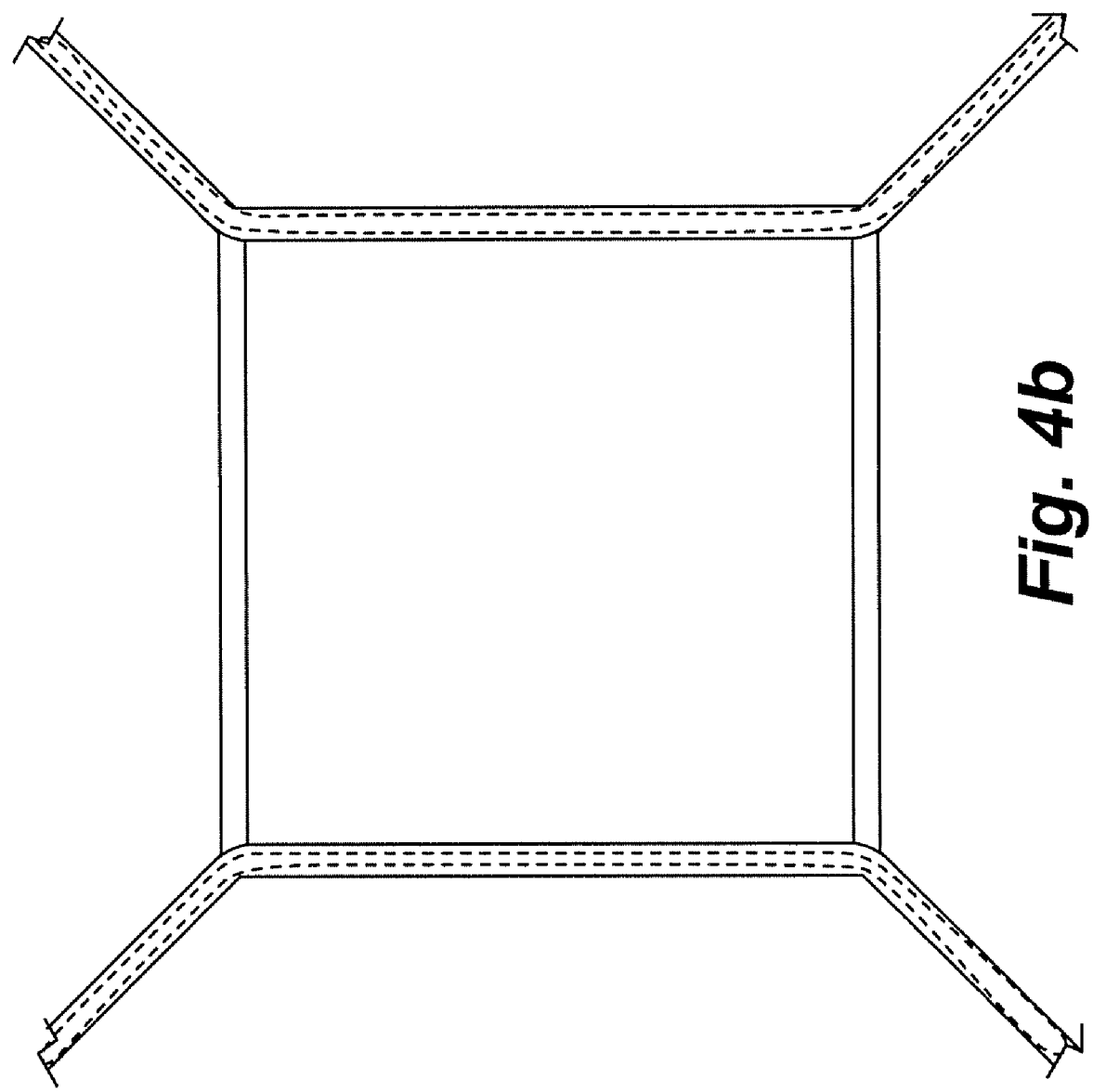
FIG. 4b depicts a flow model of fluid velocity in the first configuration of the intersection in accordance with some embodiments of the present invention.

Referring now to FIG. 3 an exemplary switching device 16 will be described in accordance with at least some embodiments of the present invention. The illustrated switching device 16 comprises a base member 38 that supports an intersection 39 of the four lines. The base member 38 may comprise retention members that secure the lines and ports to the base member 38. The intersection 39 generally resides in the center of the base member 38 and represents the common area between the four ports if no mechanism is changing the orientation of the intersection 39.

The switching device 16 further comprises one or more occlusion mechanisms 40 that are used to change the orientation of the intersection 39. Each occlusion mechanism 40a, b, in at least one embodiment, comprises a separating member 42a, b, a mount 44a, b, and a latch 46a, b. The separating member 42 is connected to the base member 38 by the mount 44 which may comprise a pivot assembly or other type of rotatable member that allows the separating member 42 to have various positions relative to the intersection 39. When the separating member 42 is in an active position (i.e., is engaged with the intersection 39), the latch 46 secures the separating member 42 to the base thus maintaining the orientation of the intersection 39. When it is desired to switch operational modes, the first latch 46a is released from the first separating member 42a and the first separating member 42a is pivoted on the first mount 44a. Thereafter, the second separating member 42b is pivoted down onto the intersection 39 and held by the second latch 46b to the base member 38. As can be appreciated by one of skill in the art, each separating member 42a, b may comprise a single separating member or two separating members that approach the intersection 39 from opposite sides and meet in the middle. If two separating members 42 are used to change the orientation of the intersection 39, the connection between ports can comprise a smoother curvature and resemble a near perfect channel.

Referring now to FIGS. 4-9, a number of configurations of the intersection 39 will be described in accordance with at least some embodiments of the present invention. The intersection 39 may comprise a square junction connecting each port of the switching device 16 as can be seen in FIGS. 4a-b. Opposing ends of the square junction may be occluded to cause blood to flow from one line to another adjacent line.

Figure 5A:
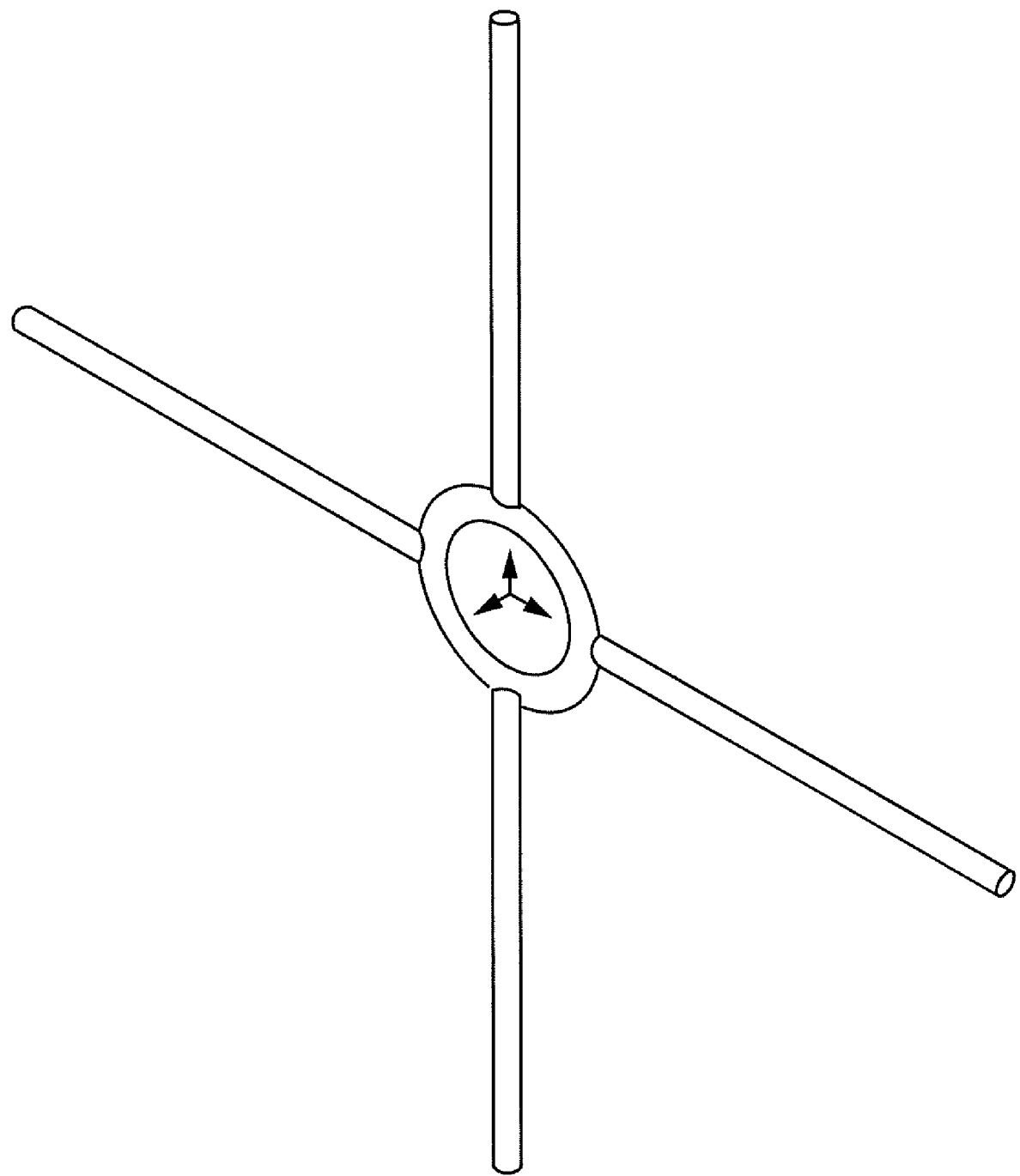
FIG. 5a depicts a second configuration of an intersection of four ports in accordance with some embodiments of the present invention.
Figure 5B:
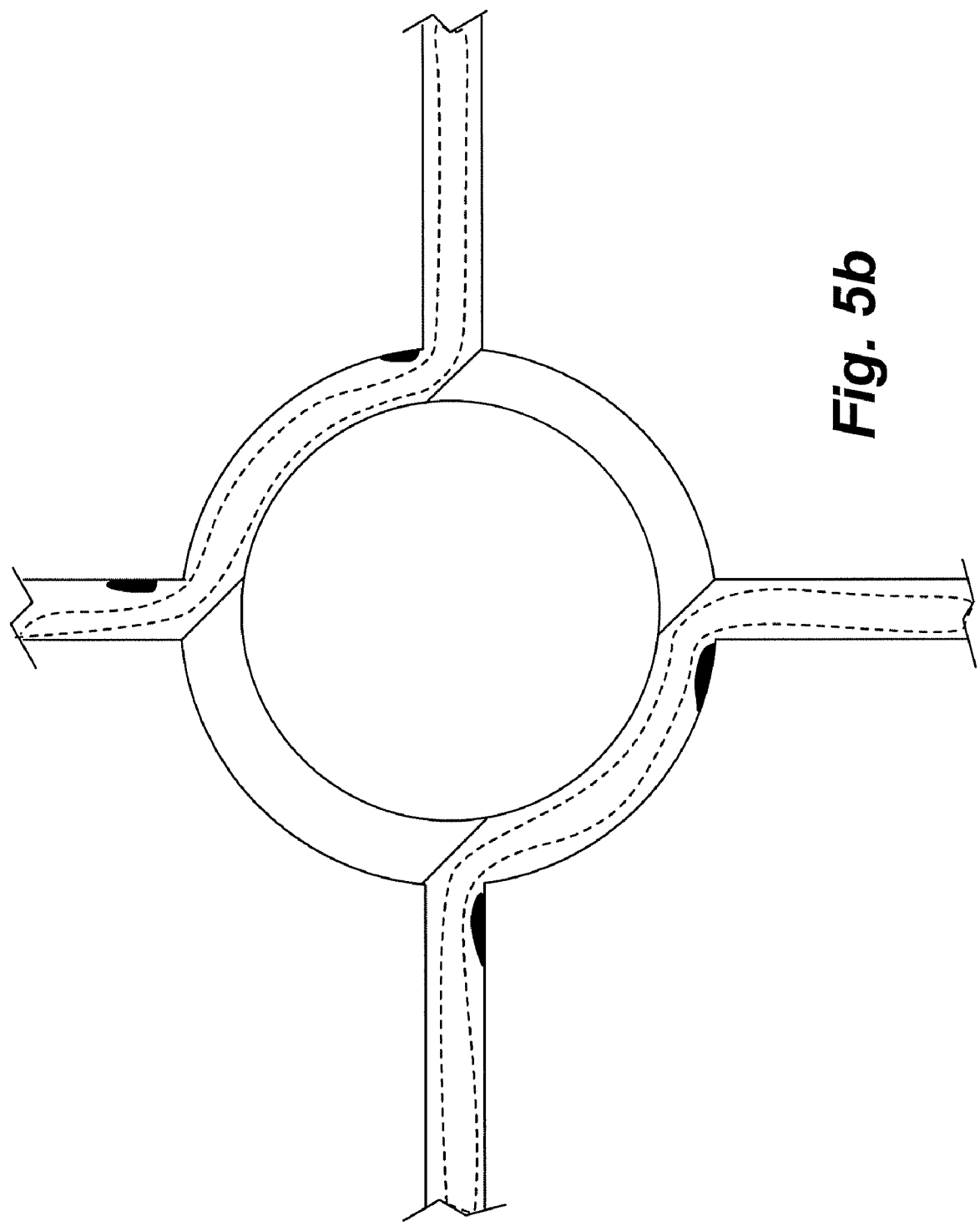
FIG. 5b depicts a flow model of fluid velocity in the second configuration of the intersection in accordance with some embodiments of the present invention.
Figure 6A:
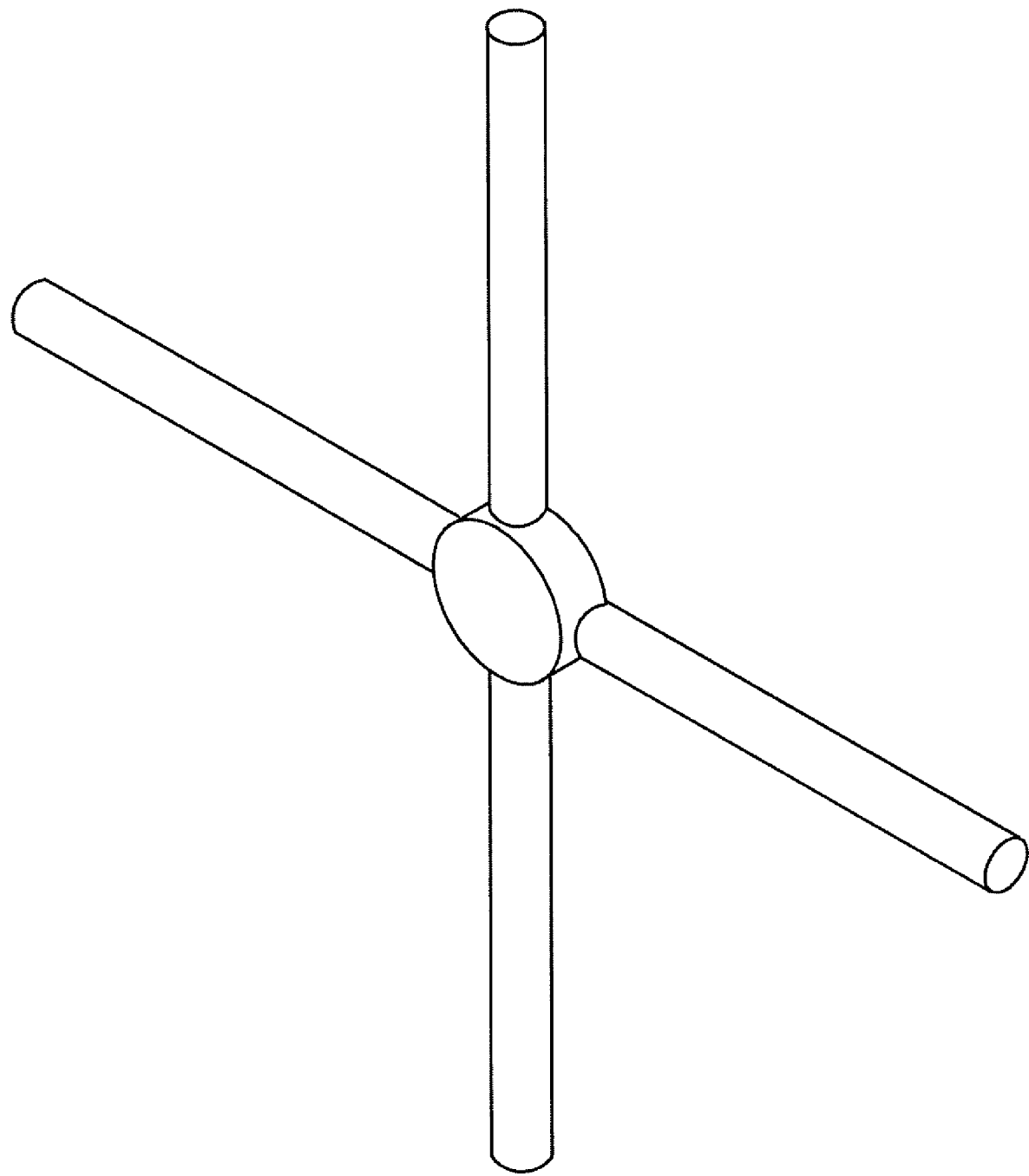
FIG. 6a depicts a third configuration of an intersection of four ports in accordance with some embodiments of the present invention.
Figure 6B:
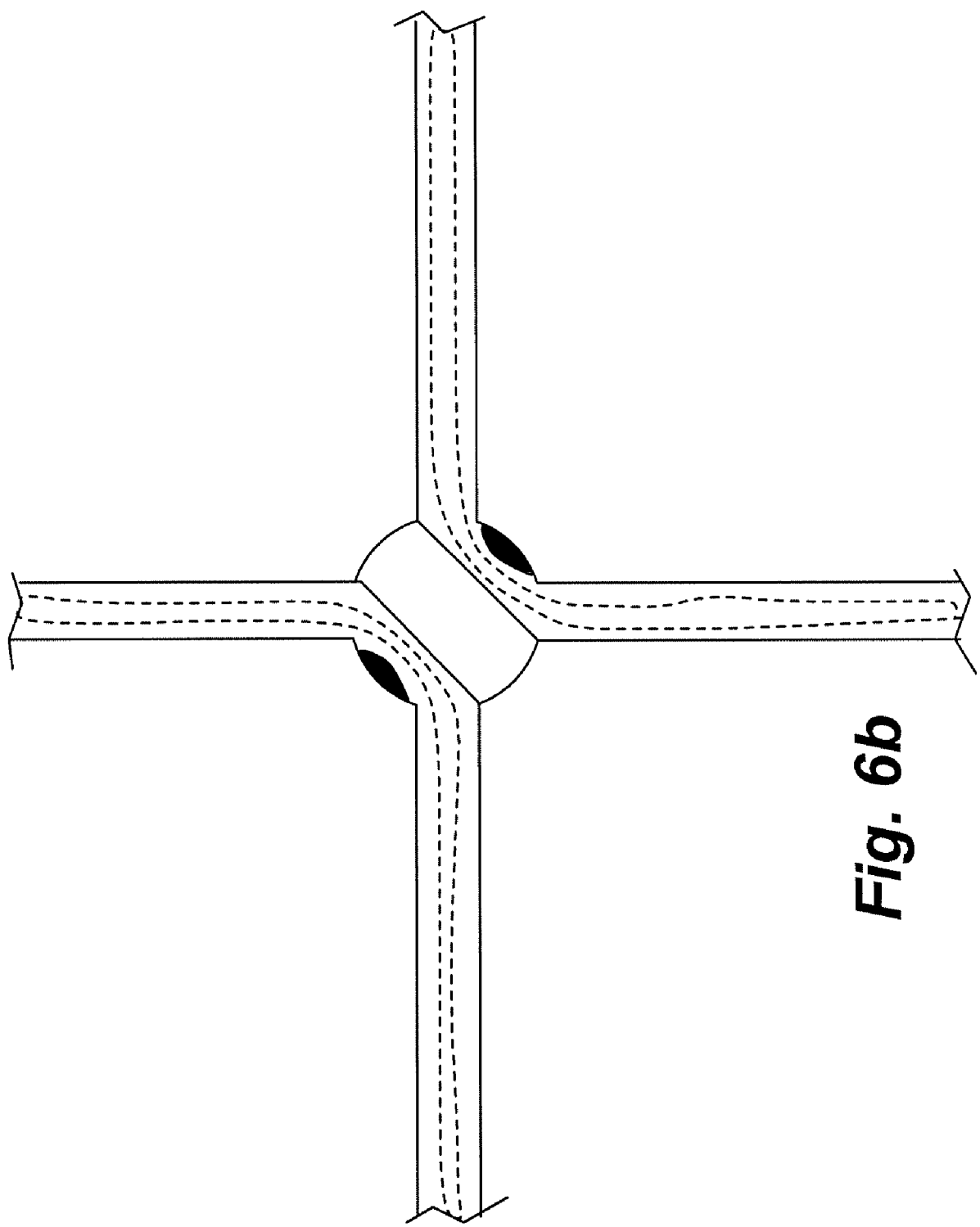
FIG. 6b depicts a flow model of fluid velocity in the third configuration of the intersection in accordance with some embodiments of the present invention.
Figure 7A:
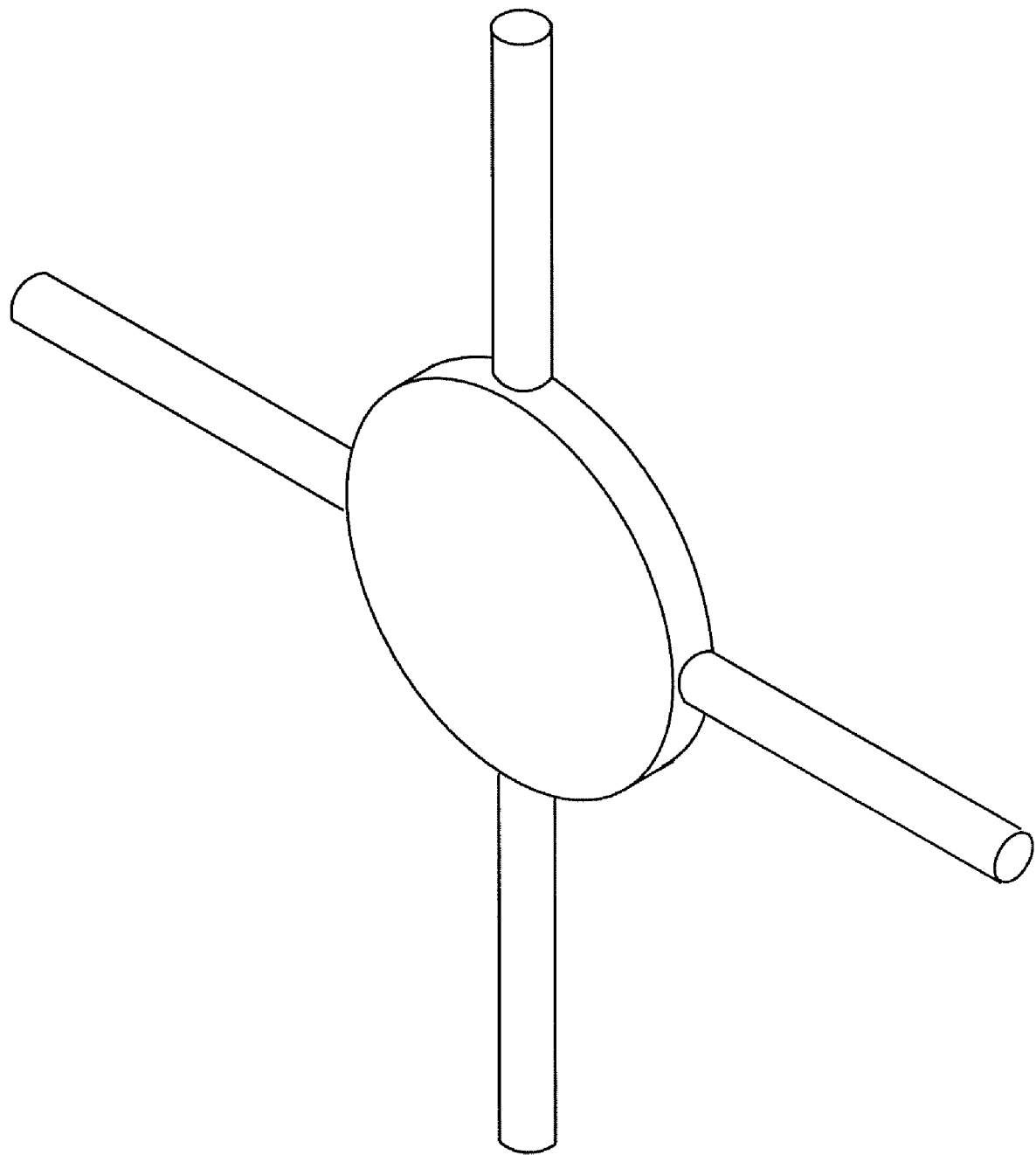
FIG. 7a depicts a fourth configuration of an intersection of four ports in accordance with some embodiments of the present invention.
Figure 7B:
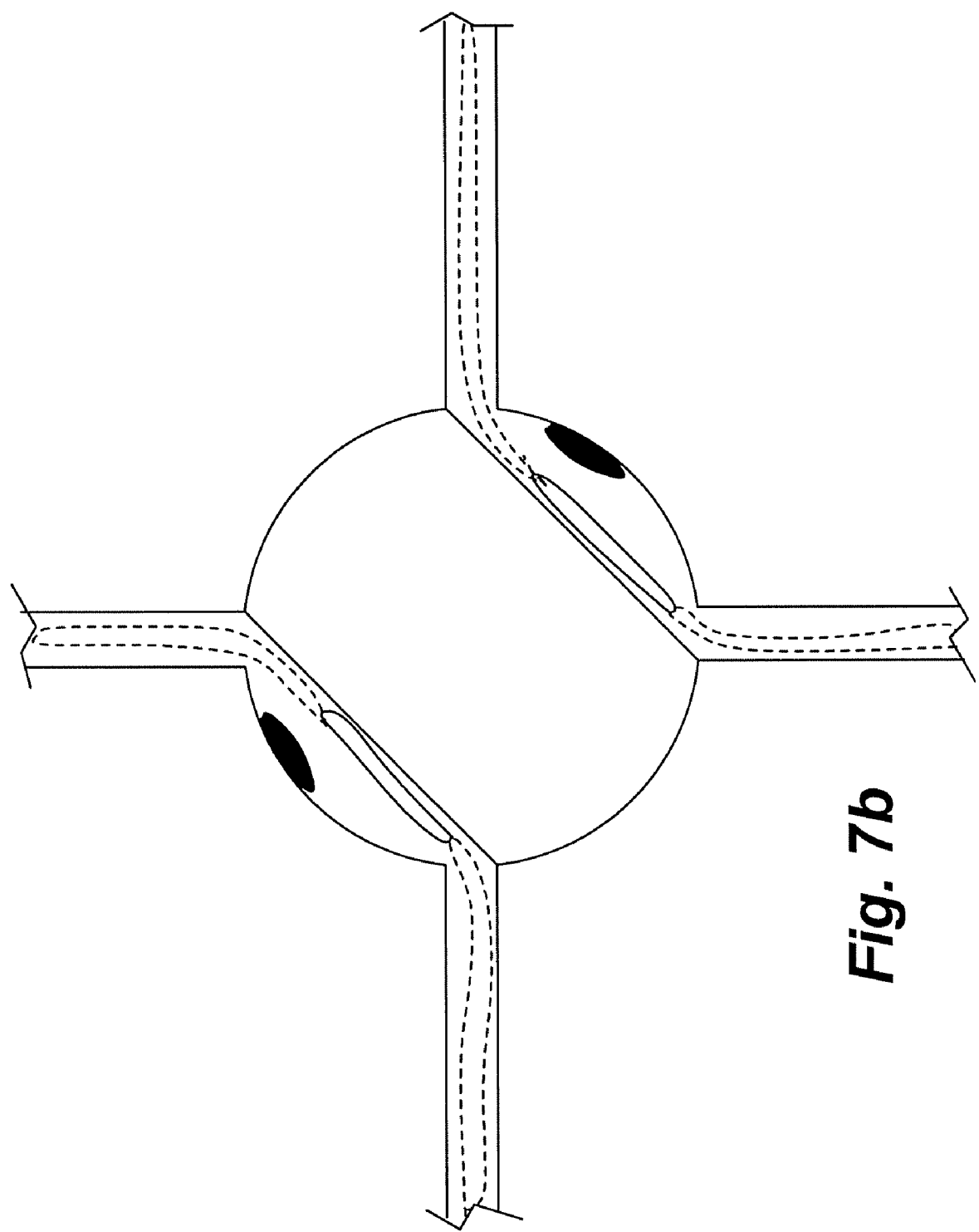
FIG. 7b depicts a flow model of fluid velocity in the fourth configuration of the intersection in accordance with some embodiments of the present invention.

In an alternative embodiment, as can be seen in FIGS. 5a-b, a circular junction resembling the perimeter of a circle is used to connect the ports of the switching device 16. Again opposing ends of the circular junction may be occluded in an operational mode causing blood to flow from one line to an adjacent line.

In a further alternative embodiment, as can be seen in FIGS. 6a-b and 7a-b, a circular reservoir or circular common area can be used to connect the ports of the switching device 16. The area is occluded such that intersection 39 substantially resembles a pipe connecting each port and any excess area of the intersection 39 is cut off from fluid flow.

Figure 8A:
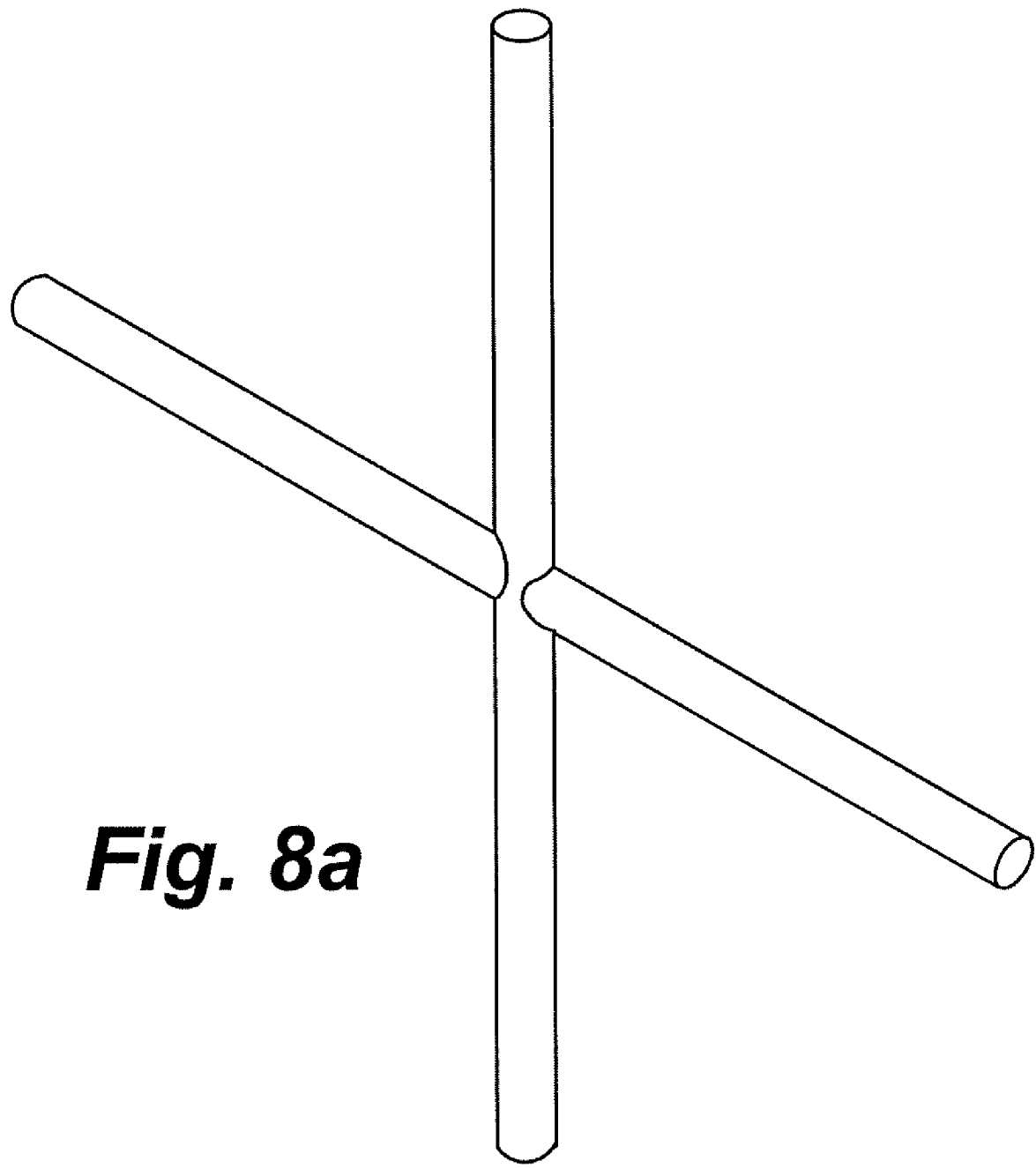
FIG. 8a depicts a fifth configuration of an intersection of four ports in accordance with some embodiments of the present invention.
Figure 8B:
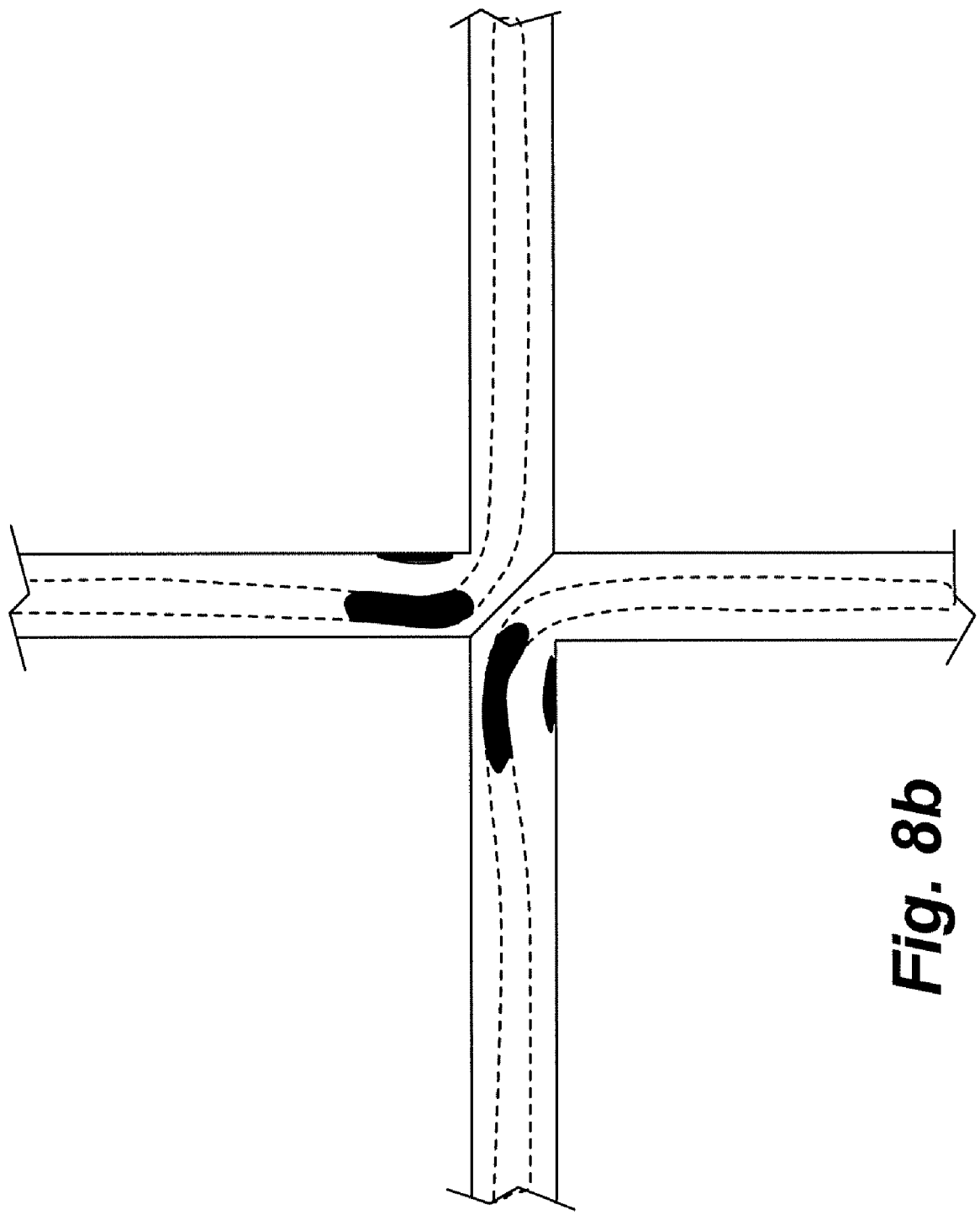
FIG. 8b depicts a flow model of fluid velocity in the fifth configuration of the intersection in accordance with some embodiments of the present invention.

In still a further embodiment, as can be seen in FIGS. 8a-b, the intersection between ports may comprise a simple t-connection. The four ports may intersect one another without any additional volume being provided at the intersection 39. In an operational mode, a separating member can be place at a diagonal to the t-intersection thus separating the intersection 39 into two sets of lines.

Figure 9A:
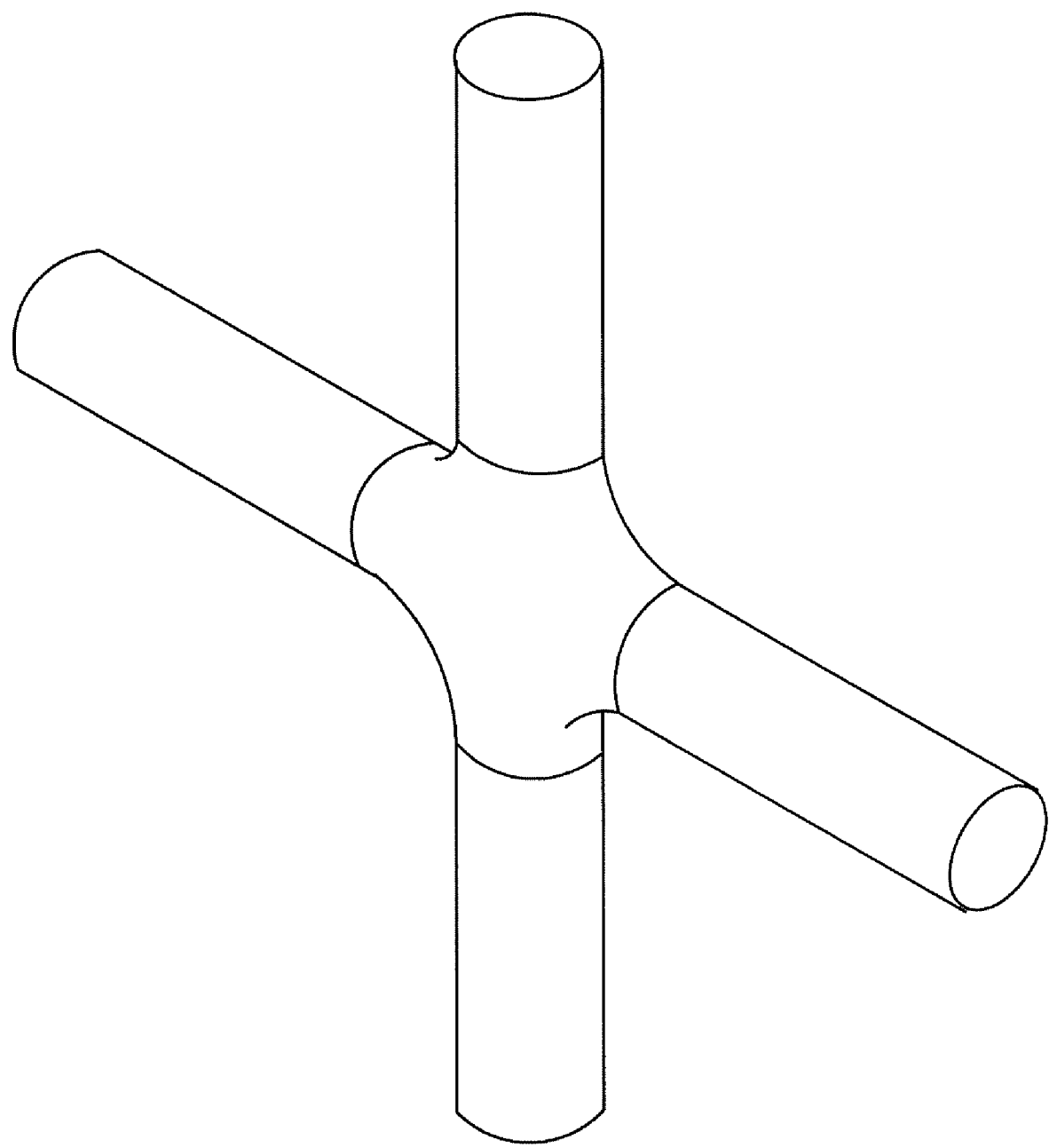
FIG. 9a depicts a sixth configuration of an intersection of four ports in accordance with some embodiments of the present invention.
Figure 9B:
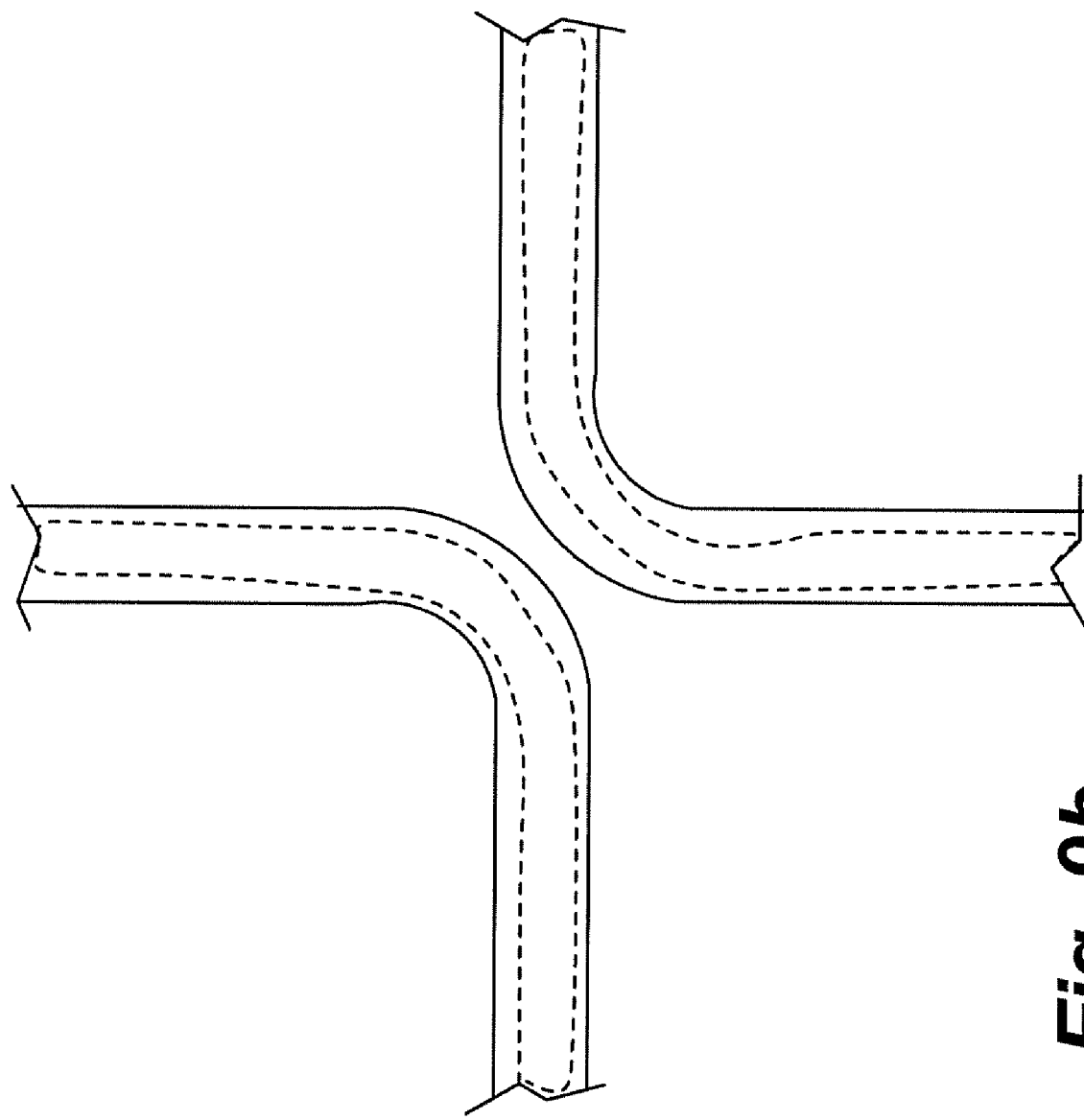
FIG. 9b depicts a flow model of fluid velocity in the sixth configuration of the intersection in accordance with some embodiments of the present invention.

Depicted in FIGS. 9a-b, yet a further embodiment of the present invention is shown. The four ports are depicted as being connected to one another at the intersection having a slightly enlarged volume and an inwardly directed radius. The inwardly directed radius creates a relatively smooth transition between adjacent ports and allows the intersection to act as a pipe when two adjacent ports are connected. More over, in the event that the separating member 42 comprises an inwardly directed radius of curvature as well, the intersection 39 can provide a smoother transition between adjacent ports. A smaller amount of stress is placed on blood cells traveling through the intersection 39 when the intersection 39 affords a smooth transition between adjacent ports. As can be appreciated by one of skill in the art, smooth transitions and a limited area for blood to remain stagnant in the intersection 39 will help ensure a safer and more effective blood flow switching device.

Figure 10:
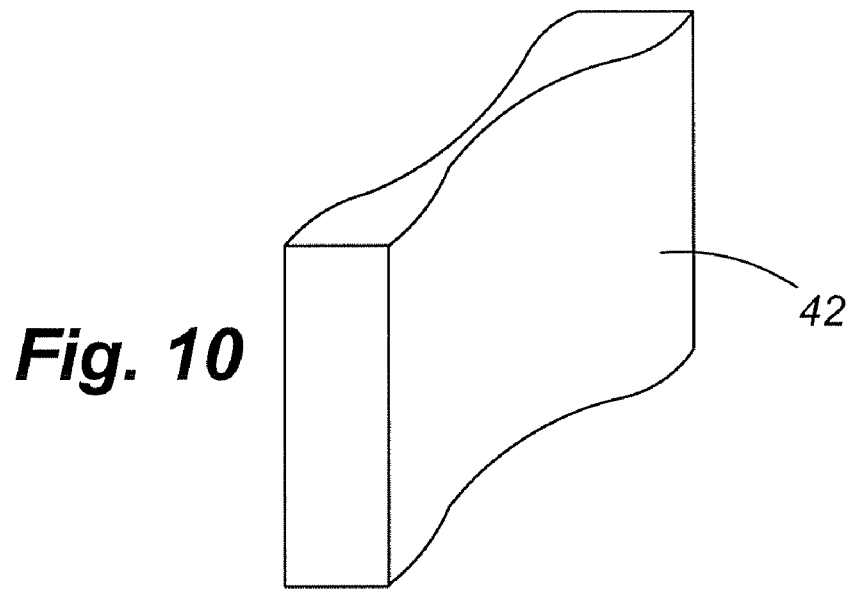
FIG. 10 is a perspective view of a separating member in accordance with at least some embodiments of the present invention.
Figure 11:
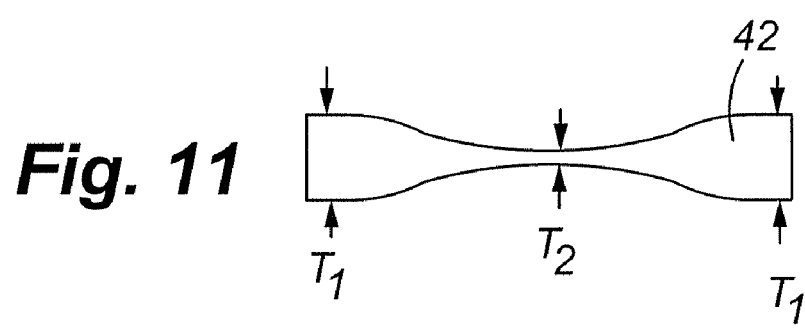
FIG. 11 is a top view of a separating member in accordance with at least some embodiments of the present invention.

Referring now to FIGS. 10-11, an exemplary separating member 42 is depicted in accordance with at least some embodiments of the present invention. The separating member 42 may comprise an inwardly directed radius of curvature that helps create a smooth transition between ports when the separating member 42 is engaged with the intersection 39. The separating member 42 comprises first and second ends that are connected by a middle portion.

FIG. 11 depicts a cross-section of the separating member 42 along line 10-10. The thicknesses of the first and second ends $T_1$ are relatively thicker than the thickness of the middle portion $T_2$. A smooth transition between the ends through the middle portion helps direct blood flows without a radical change of direction.

Figure 12:
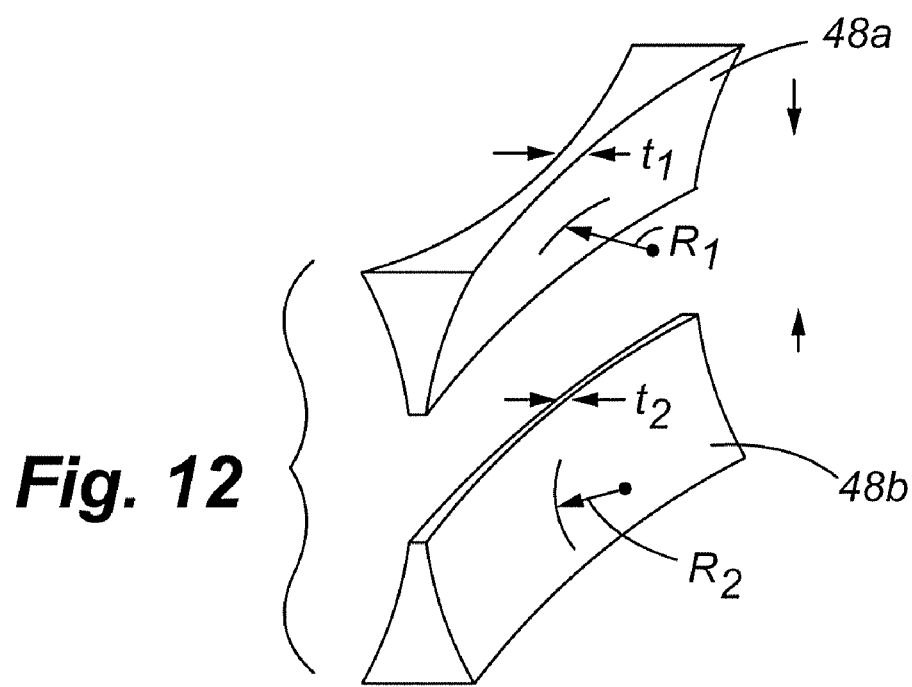
FIG. 12 is a perspective view of a pair of separating members in accordance with at least some embodiments of the present invention.

Referring now to FIG. 12, a pair of separating members 48a and 48b will be described in accordance with at least some embodiments of the present invention. The separating member 48 can be used to engage the intersection 39 at opposite side. In other words, the first separating member 48a can engage the top side of the intersection 39 whereas the second separating member 49a can engage the bottom side of the intersection 39. When the separating members 48 are brought together, a smooth transition between ports in the intersection 39 is created. To further create a smooth transition in the intersection 39, the side of the separating member 48 that engages the intersection 39 may have a different thickness than the side of the separating member 48 that does not engage the intersection 39. Stated in another way, the non-engaging side of the separating member 48 may have a first thickness of $t_1$ whereas the engaging side of the separating member 48 may have a second thickness of $t_2$. The smooth transition between the top and bottom sides of the separating member 48 may further help create a smooth transition between ports in the intersection 39.

As can be seen from the illustration of FIG. 12, each of the separating members 48a and 48b may comprise more than one radius of curvature. More specifically, the separating member 48 may comprise a first radius of curvature $R_1$ in a first plane that is substantially parallel to the top and/or bottom plane of the separating member 48. The separating member 48 may further comprise a second radius of curvature $R_2$ that is substantially orthogonal to the first radius of curvature $R_1$. In one embodiment, the tubing is used to carry blood or the like during hemodialysis and comprises an outer diameter between about 5 mm and 8 mm. If such tubing is used, the first radius $R_1$ of the separating member 48 may be between about 10 mm and about 30 mm. The second radius $R_2$ of the separating member 48 may be between about 2 mm and about 5 mm. In a preferred embodiment, the second radius $R_2$ substantially equals the outer radius of the tubing used to carry the fluid. Therefore, when the two separating members 48 are brought together, a cross-section of their intersection substantially resembles a tube. Thus, when two separating member 48 are brought together at an intersection 39, a smooth transition is created between adjacent ports. The transition at the intersection 39 between ports is fashioned to allow blood to flow from one port to an adjacent port at a velocity between about 0.2 m/s and about 0.6 m/s through the main channel of the line, with preferred velocities ranging between about 0.2 m/s and 0.4 m/s. The smooth transition creates a relatively small range in overall fluid velocities, which helps mitigate blood clots at the intersection 39 and excessive fluid forces (on the blood cells and tube walls) due to accelerations in the intersection. Essentially, the blood undergoes a centripetal acceleration due to the change in direction but undergoes little to no impact forces at the transition.

Figure 13A:
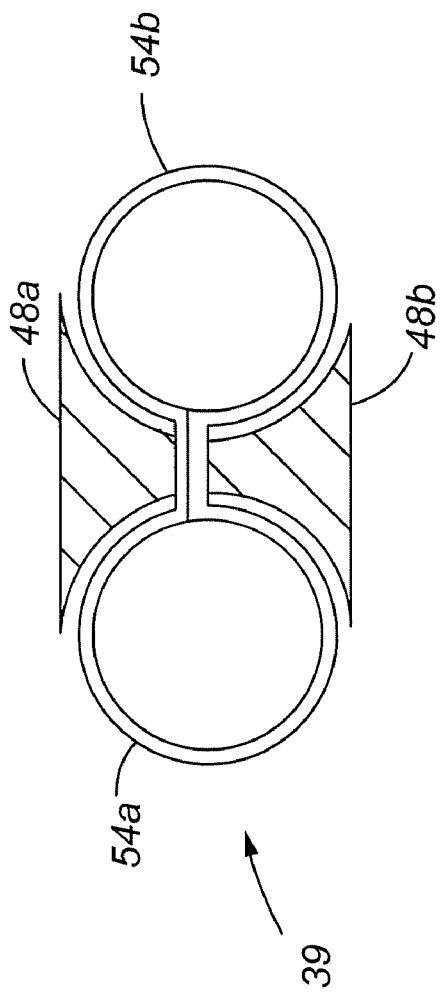
FIG. 13a is a cross-sectional view of a pair of separating members engaging an intersection in accordance with at least some embodiments of the present invention.
Figure 13B:
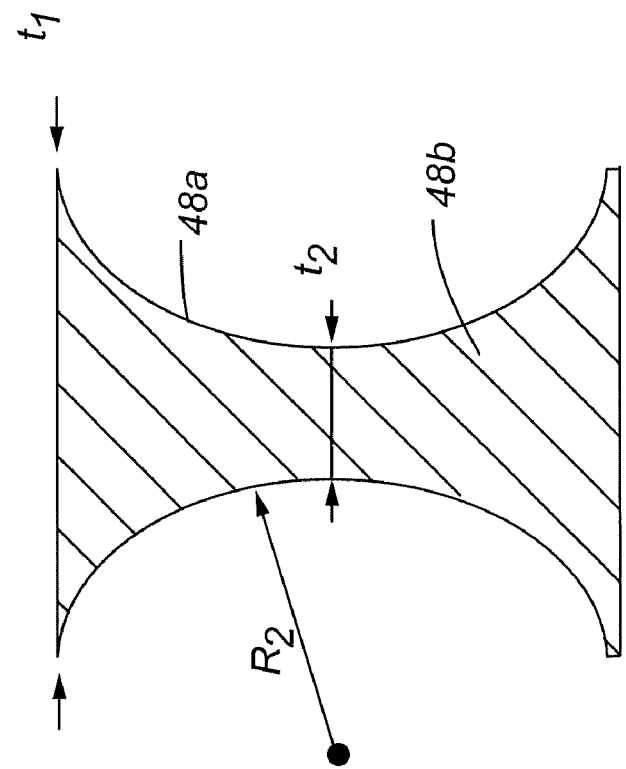
FIG. 13b is a cross-sectional view of a pair of separating members in accordance with at least some embodiments of the present invention.

With reference now to FIGS. 13a and 13b, the operation of a pair of separating members 48 will be described in accordance with at least some embodiments of the present invention. When the pair of separating members 48 are brought together about the intersection 39, two passageways 54a and 54b are created for the fluid to flow through. Specifically, in accordance with one embodiment, the first passageway 54a carries the blood from the patient access 36 to the filter 28. The second passageway 54b carries the blood from the filter 28 back to the patient access 36. The separating members 48 engage the intersection 39 such that each passageway 54 is a nearly perfect conduit for fluid. There are no substantially sharp angles created in the passageway 54 that may otherwise damage or trap blood cells.

A relatively smooth inwardly directed radius of curvature $R_2$ is created when the two separating members 48 engage one another, as can be seen in FIG. 13b. The radius is created as a result of the outer surface of the separating member 48 tapering from a first thickness $t_1$ at its widest point to a second thickness $t_2$ at its skinniest point. The transition between the widest point of the separating member 48 and the skinniest point has a smooth transition that helps form the passageways 54 into relatively cylindrical shapes.

Figure 14:
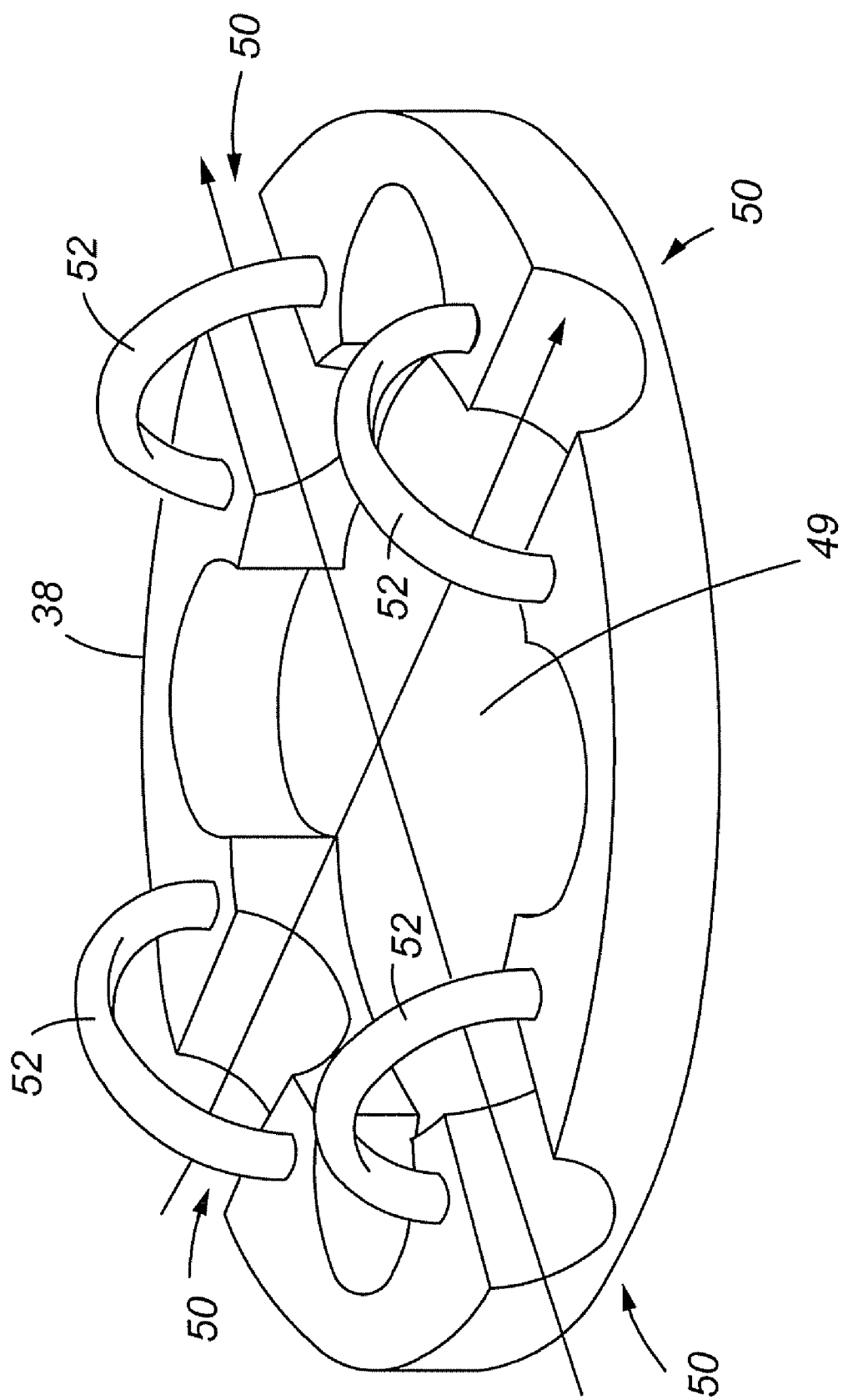
FIG. 14 is a perspective view of a base member in accordance with at least some embodiments of the present invention.

FIG. 14 illustrates a base member 38 which can be, but does not have to be used to retain an intersection 39 and lines connected thereto. The base member 38 comprises a center portion 49 for receiving the intersection 39. The center portion 49 may include an open space or cavity as shown in FIG. 13 or may comprise a planar surface on which the intersection 39 can rest. The base member 38 further comprises a number of line/port receivers 50 each of which has a corresponding retainer 52. The base member 38 and its associated elements may be constructed of any suitable material including, without limitation, plastic, metal, composites, and the like. The base member 38 functions to retain the intersection 39 in a relatively stable position relative to an occlusion mechanism 40 that can ultimately be used to control blood flow through the intersection 39.

Figure 15:
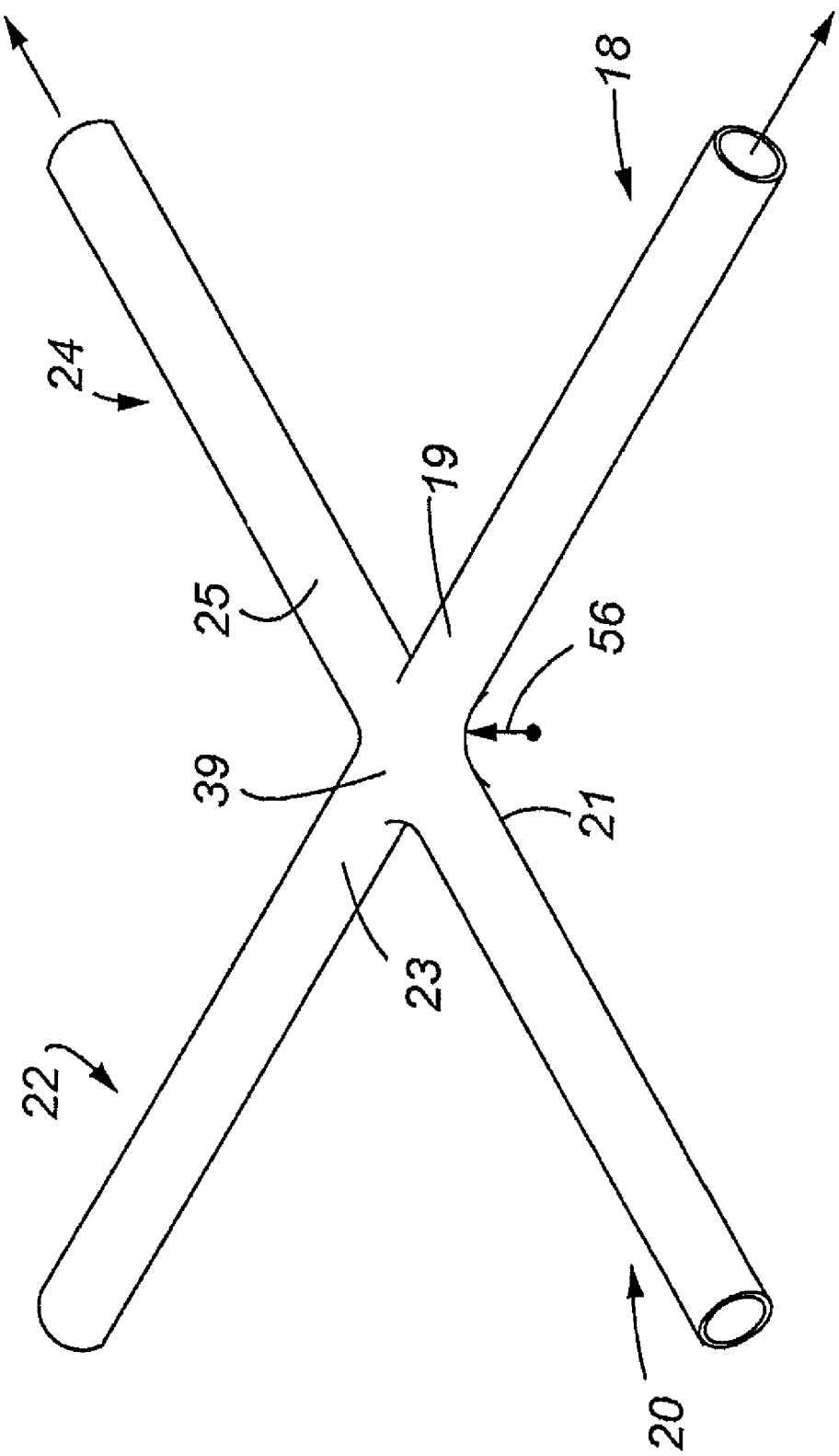
FIG. 15 is a perspective view of an intersection in accordance with at least some embodiments of the present invention.

Referring now to FIG. 15, an exemplary intersection 39 will be described in accordance with at least some embodiments of the present invention. As previously noted, the intersection 39 serves as a single junction between four ports 19, 21, 23, and 25. The ports correspond to lines 18, 20, 22, and 24 that carry fluid in the extracorporeal circuit. The transition between adjacent ports comprises a radius of curvature 54 that helps the fluid flow smoothly between ports without creating any substantial eddies or points of stagnation. The materials used to create the intersection 39, ports, and lines may be any suitable type of material including, for example, plastics or other polymers, glass, metal, and the like. In a preferred embodiment, the intersection 39, ports, and lines are constructed of a plastic material (i.e., PVC, polyethylene, or similar polymer) that is biocompatible, meaning that it does not adversely affect biomaterial (e.g., blood) passed through the tubing.

In accordance with one embodiment, the inner diameter of tubing used ranges between about 4 mm and 10 mm, with a more preferred range being between about 5 mm and about 8 mm, and a most preferred diameter of 6 mm tubing. The inwardly directed radius of curvature 56 of the intersection 39 can range between about 5 mm and about 15 mm with a preferred radius being about 10 mm for 6 mm inner diameter tubing.

In one embodiment, the intersection 39, ports, and lines are formed of a single continuous material, meaning there are no intersections or joints between elements. In another embodiment, the tubing is a separate element from the intersection 39 and is connected to the intersection 39 via the ports. The connection between lines and ports may include a frictional fit intersection where the lines have an outer radius that is slightly smaller than the inner radius of the ports, thus allowing the port to receive the line. Alternatively, the outer radius of the port may be slightly smaller than the inner radius of the line, thus allowing the line to receive the port. Still further in the alternative, the tubing and ports may have a similar radius and may be connected by a connecting mechanism.

In accordance with one embodiment, two sides of the intersection 39 corresponding to two adjacent ports may have a first color or texture and the other two sides of the intersection 39 may have a second color or texture. The material of the intersection 39 may be given a particular type of pigment that allows the attendant and/or doctor to know whether the system is currently flowing in the normal direction or has a reversed flow. In one embodiment, if a separating member 48 divides the intersection 39 to cause normal flow in the extracorporeal circuit, adjacent ports of similar colors are connected (i.e., the two red ports are connected and the two blue ports are connected). If the intersection 39 is later divided to cause a reversal of flow, adjacent ports of dissimilar colors would be connected (i.e., a red port would be connected to a blue port for each pair of ports). Using a color-coded scheme the attendant can easily determine what direction the fluid is flowing through the extracorporeal circuit by simply looking at the intersection 39. The ports can alternatively and additionally be marked by letters of the alphabet, like for instance AP, AM, VP and VM to allow for easy recognition of where the ports are assigned to.

Figure 16:
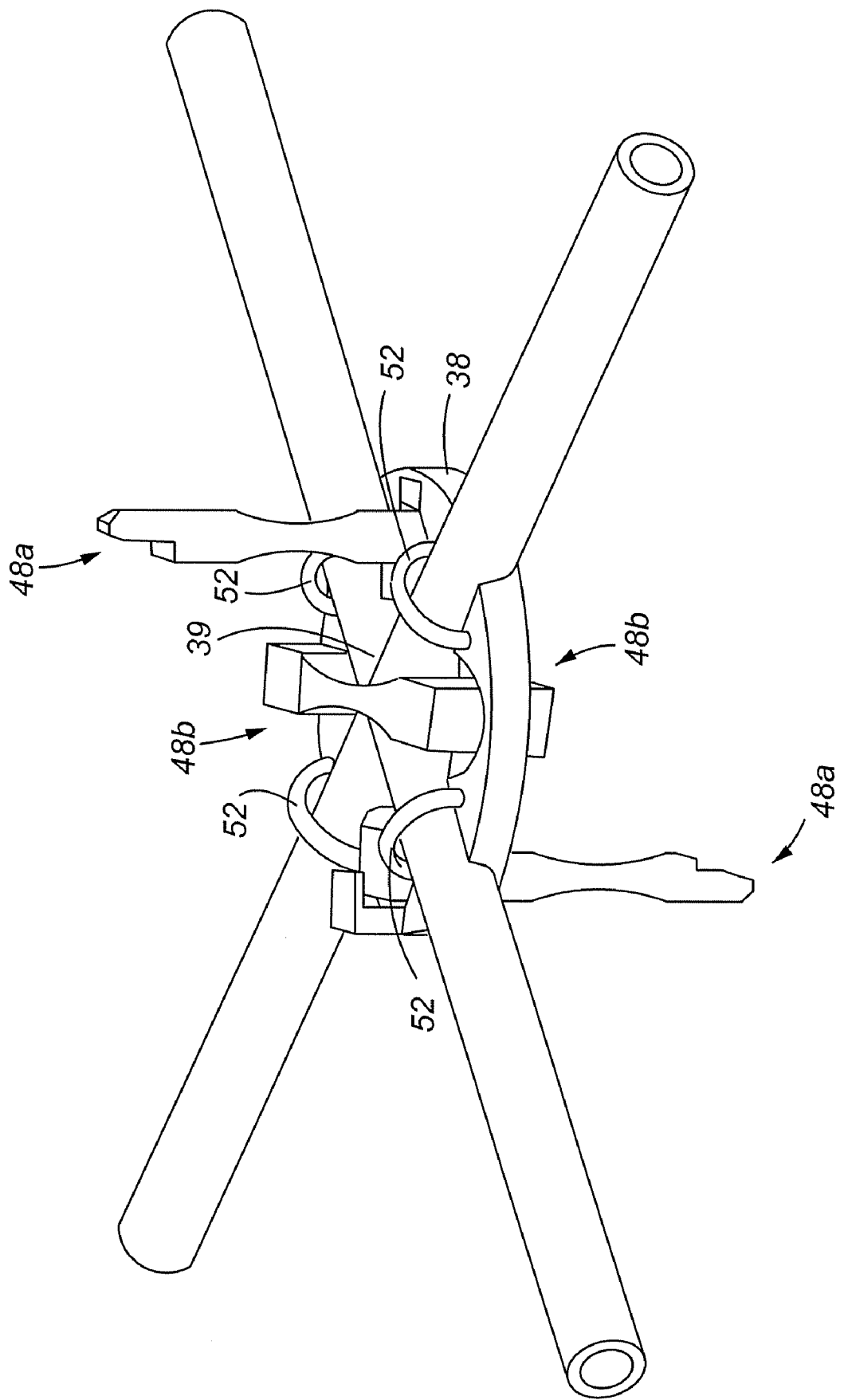
FIG. 16 is a perspective view of a switching device employing two sets of separating members in accordance with at least some embodiments of the present invention.

FIG. 16 depicts a switching device 16 comprising a pair of separating members 48 that are used to occlude the intersection 39 from two directions. Specifically, the top separating member and bottom separating member may be connected to the base member 38 in a similar fashion to that discussed above. Namely, the separating members may be hingedly attached to the base member 38 such that they can be moved to engage the intersection 39 with relative ease. The switching device 16 may comprise a first set of separating member 48*a* that divide the intersection 39 in one direction and a second set of separating members 48*b* that divide the intersection in a different direction. The first set of separating members 48*a* may have a first color or other defining attribute that differentiates them from the second set of separating member 48*b*. Therefore, if a red set of separating members 48 are engaging the intersection 39, then the attendant can determine that the flow is reversed. Whereas if a blue set of separating members 48 are engaging the intersection 39, then the attendant can determine that the flow is not reversed.

The clamping mechanism can also be a single clamp, made of two connected and uniquely formed prongs as described in FIGS. 10-13. The clamping mechanism can be reusable or disposable depending upon the desired application.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for switching the direction of fluid flow, comprising:
    an intersection between a first, second, third, and fourth port;
    an occlusion mechanism having a first and second radius of curvature for operatively adapting the intersection such that in a first position, the first and second ports are fluidically connected by the intersection and the third and fourth ports are fluidically connected by the intersection and in a second position, the first and fourth ports are fluidically connected by the intersection and the second and third ports are fluidically connected by the intersection;
    wherein the occlusion mechanism comprises a separating member external to fluid flow and does not directly contact a fluid having a first and second end with a middle portion having at least one curved surface there between, and wherein the thicknesses of the first and second ends are larger than the thickness of the middle portion.

2. The device of claim 1, wherein the radius of curvature of the separating member is inwardly directed such that a continuously smooth transition is created between at least two of the first, second, third, and fourth ports when the separating member is engaged with the intersection.

3. The device of claim 1, wherein when the occlusion mechanism is in the first position the first and third ports are inlet ports to the intersection and the second and fourth ports are outlet ports from the intersection, and wherein when the occlusion mechanism is in the second position the third and fourth ports are inlet ports to the intersection and the first and second ports are outlet ports from the intersection.

4. The device of claim 1, wherein the occlusion mechanism comprises a first and second separating member, each of which have an inwardly directed radius of curvature, and wherein the first separating member operatively engages the intersection in the first position and the second separating member operatively engages the intersection in the second position.

5. The device of claim 1, wherein the intersection comprises an inwardly directed radius of curvature between at least two of the first, second, third, and fourth ports, wherein the inwardly directed radius of curvature creates a continuously smooth transition between adjacent ports; and wherein the inwardly directed radius of curvature reduces the amount of stress on blood cells traveling through the intersection.

6. The device of claim 1, wherein the first and fourth ports are substantially aligned with a common first axis and wherein the second and third ports are substantially aligned with a common second axis.

7. The device of claim 6, wherein the first and second axes are substantially orthogonal to one another.

8. The device of claim 1, wherein the first, second, third, and fourth ports and the intersection substantially lie in a first plane and wherein the occlusion mechanism engages the intersection from a direction substantially perpendicular to the first plane.

9. The device of claim 8, wherein the radius of curvature of the occlusion mechanism is at least in the first plane.

10. The device of claim 1, wherein the separating member further comprises: a top surface and a bottom surface, wherein the thickness of the top surface conforms to the curved surface between the first and second ends, and wherein the top surface operably engages a top side of the intersection and the bottom surface operably engages a bottom side of the intersection.

11. The device of claim 1, wherein the ports are color coded to indicate fluid flow in the first and second position.

12. The device of claim 1, wherein the ports are marked with characters to indicate fluid flow in the first and second position.

13. A hemodialysis machine, comprising:
a device for switching fluid flow comprising:
an intersection between a first, second, third, and fourth port; and
an occlusion mechanism having a first and second radius of curvature for operatively adapting the intersection such that in a first position, the first and second ports are fluidically connected by the intersection and the third and fourth ports are fluidically connected by the intersection and in a second position, the first and fourth ports are fluidically connected by the intersection and the second and third ports are fluidically connected by the intersection;
wherein the occlusion mechanism comprises a separating member external to fluid flow and does not directly contact a fluid having a first and second end with a middle portion having at least one curved surface there between, and wherein the thicknesses of the first and second ends are larger than the thickness of the middle portion.

14. The hemodialysis machine of claim 13, further comprising a switching mechanism for changing the position of the occlusion mechanism between the first and second positions.

15. The hemodialysis machine of claim 14, device comprises at least one of a button, lever, switch, and touch screen that can be actuated to change the position of the occlusion mechanism between the first and second positions.

16. The hemodialysis machine of claim 14, device causes the occlusion mechanism to temporarily change positions, thereby reversing fluid flow.

17. The hemodialysis machine of claim 16, wherein said fluid flow comprises blood fluid flow and wherein when the position of the occlusion mechanism is temporarily changed such that said patient's blood flow can be measured.

18. The hemodialysis machine of claim 14, wherein said switching mechanism changes the position of the occlusion mechanism automatically.

19. The hemodialysis machine of claim 18, wherein said switching mechanism changes position in response to receiving an electronic signal from an external device.

20. The hemodialysis machine of claim 13, wherein the occlusion mechanism creates channels between adjacent ports in both the first and second positions and wherein the channels facilitate substantially laminar fluid flows between adjacent ports.

21. The hemodialysis machine of claim 13, wherein said occlusion mechanism comprises at least one separating member having at least one inwardly directed radius of curvature such that a continuously smooth transition is created between at least two of the first, second, third, and fourth ports when the separating member is engaged with the intersection, and wherein the inwardly directed radius of curvature reduces the amount of stress on blood cells traveling through the intersection.

22. The hemodialysis machine of claim 21, wherein said at least one separating member comprises a first radius of curvature and a second radius of curvature and wherein the first and second radiuses of curvature do not lie in a common plane, and wherein the at least one separating member further comprises a top surface and a bottom surface, wherein the thickness of the top surface conforms to the curved surface between the first and second ends, and wherein the top surface operably engages a top side of the intersection and the bottom surface operably engages a bottom side of the intersection.

23. The hemodialysis machine of claim 22, wherein said first and second radiuses of curvature are substantially orthogonal to one another.

24. A method of controlling fluid flow through a fluidic intersection having a first, second, third, and fourth port, the method comprising:
engaging the fluidic intersection with an occlusion member in a first position thereby causing fluid to flow from the first port to the second port and from the fourth port to the third port;
wherein the occlusion member comprises an inwardly directed a first and second radii of curvature that helps create a continuously smooth transition between ports such that the fluid flows in a substantially laminar fashion; and
wherein the occlusion mechanism comprises a separating member external to fluid flow and does not directly contact a fluid having a first and second end with a middle portion having at least one curved surface there between, and wherein the thicknesses of the first and second ends are larger than the thickness of the middle portion.

25. The method of claim 24, wherein the fluid flows between ports with a velocity ranging between about 0.2 m/s and about 0.6 m/s.

26. The method of claim 24, further comprising changing the position of the occlusion member to a second position thereby causing fluid to flow from the third port to the second port and from the fourth port to the first port.

27. The method of claim 24, wherein the fluid comprises blood cells and wherein the continuously smooth transition limits the impact forces endured by the blood cells as they pass through the intersection below the forces required to break blood cells.

28. A device for switching the direction of blood flow in a patient during the process of hemodialysis, comprising:
an intersection between a first, second, third, and fourth port, wherein each port has an inner radius of curvature between about 5 mm and about 8 mm;
an occlusion mechanism having a first radius of curvature in a first plane between about 10 mm and about 30 mm and a second radius of curvature in a second plane substantially orthogonal to said first plane between about 2 mm and about 5 mm, wherein the occlusion mechanism engages the intersection such that in a first position, the first and second ports are fluidically connected by the intersection and the third and fourth ports are fluidically connected by the intersection and in a second position, the first and fourth ports are fluidically connected by the intersection and the second and third ports are fluidically connected by the intersection
wherein the occlusion mechanism comprises a separating member external to fluid flow and does not directly contact a fluid.

* * * * *